US006303125B1

(12) United States Patent
Ofek et al.

(10) Patent No.: US 6,303,125 B1
(45) Date of Patent: *Oct. 16, 2001

(54) ANTI-MICROBIAL-ADHESION FRACTION DERIVED FROM VACCINIUM

(75) Inventors: Itzhak Ofek, Givataun; Ervin Weiss, Herzeliya; Yoel Kashman, Tel Aviv; Janina Goldhar, Tel Aviv; Nathan Sharon, Tel Aviv, all of (IL)

(73) Assignee: RAMOT-University Authority for Applied Research and Industrial Development Ltd., Ramat-Aviv, Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/159,626

(22) Filed: Sep. 24, 1998

Related U.S. Application Data

(63) Continuation-in-part of application No. 08/772,021, filed on Dec. 19, 1996, now Pat. No. 5,840,322.

(51) Int. Cl.[7] .................................................. A01N 65/00
(52) U.S. Cl. ...................... 424/195.1; 424/405; 424/408; 424/410; 424/417; 424/440; 514/783
(58) Field of Search ................................ 424/195.1, 405, 424/408, 410, 417, 440; 514/783

(56) References Cited

U.S. PATENT DOCUMENTS 5,525,341 * 6/1996 Walker et al. ..................... 424/195.1
5,840,322 * 11/1998 Weiss et al. ........................... 424/405

OTHER PUBLICATIONS

"Toward Adhesion Therapy for Microbial Diseases" (Kahane/Ofek: NY Plenum Press) pp 179–83, 1996.*
Boren and Falk, 1995. Helicobacter pylori binds to blood group antigens. Scientific American Science and Medicine. Sep./Oct. 28–37. N/A—will send.
Burger et al., 1998. High Molecular weight constituent of cranberry juice inhibits the adhesion of *Heliobacter Pylori* to human gastric mucin. Abstract, 11th Mediterranean Congress of Chemotherapy, Tel Aviv. N/A—will send.
Cover and Blaser, *Helicobacter pylori:* a bacterial cause of gasrtritis, peptic ulcer disease, and gastric cancer. A. S. M. News 61:21–26. N/A—will send.
Folin and Denis, 1912. On phosphotungstic–phophomolybdic compounds as color reagents. J. Biol. Chem. 12:239–243.
Germaine et al., 1974. Rapid filter paper assay for the dextransucrase activity from *Streptococcus mutans*. J. Dent. Res. 53 (6): 1355–1360.
Helrich (editor), 1990. Official Methods of Analysis of the Association of Official Analytical Chemists. p. 703, section 952–03.
Lee A, Fox J, and Hazell S. 1993. Pathogenicity of *Helicobacter pylori:* a perspective. Infect. Immun. 61: 1601–1610. N/A—will send.
Mehansho et al., 1987. Dietary tannins and salivary prolin-–rich proteins: Interactions, induction, and defense mechanisms. Ann. Rev. Nur. 7: 423–440.
Ofek, et al., 1996. Toward anti–adhesion therapy for microbial diseases. Trends Microbiol. 4: 297–299.
Terleckyj, et al., 1975. Growth of several cariogenic strains of oral streptococci in chemically defined medium. Infect. Immun. 11(4): 649–655.

* cited by examiner

Primary Examiner—Bennett Celsa
(74) Attorney, Agent, or Firm—Kohn & Associates

(57) ABSTRACT

A non-food anti-microbial-adhesion and aggregation composition comprising a suitable carrier and an effective amount of an adhesion inhibitory fraction isolated from juice from berries of the Vaccinium plant genus. In an embodiment the anti-aggregation and adhesion fraction is isolated from cranberry juice. It is characterized as being polymeric and having a molecular weight $\geq 14,000$; an elemental analysis of carbon 43–51%, hydrogen 4–5%, no nitrogen, no sulfur and no chlorine; a nuclear magnetic resonance (NMR) line spectrum as set forth in FIGS. 2A and 2B; and an ultraviolet spectrum with an absorption peak at 280 nm in neutral or acidic pH solution which is absent in alkali solutions. This fraction exhibits adhesion inhibitory activity against P fimbriated bacteria, oral bacteria and *Helicobacter pylori*.

3 Claims, 8 Drawing Sheets

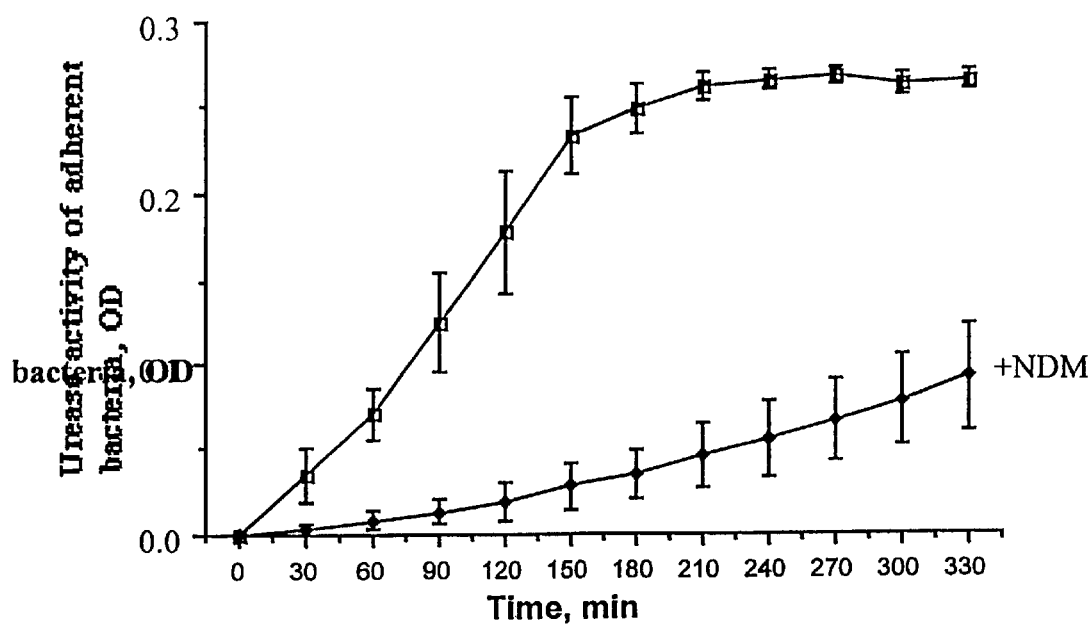
Fig 9. Effect of NDM of adhesion of *Helicobacter pylori* to human gastric mucin.

US 6,303,125 B1

ANTI-MICROBIAL-ADHESION FRACTION DERIVED FROM VACCINIUM

CROSSREFERENCE TO RELATED APPLICATIONS

This application is a Continuation-In-Part of U.S. Pat. No. 5,840,332, filed Dec. 19, 1996.

BACKGROUND OF THE INVENTION

1. Technical Field

This invention relates to plant extracts having therapeutic and other uses, and more specifically to an extract of juice from berries of the Vaccinium plant genus having an anti-microbial-adhesion activity.

2. Background Art

Adhesion of the bacteria to each other (intraspecies) and to other bacterial species (intergeneric coaggregation) as well as to host tissues and cells contributes significantly to disease progression and pathology as for example in dental caries and plaque as well as in the persistance of Helicobacter pylori infection. It would therefore be useful to have compounds which can interrupt microbial adhesion and aggregation.

Chronic ulcers have been shown to be caused by Helicobacter pylori and the presence of chronic ulcers is associated frequently with complications leading to gastric cancer [Cover and Blaser, 1995]. H. pylori, first isolated from a specimen of gastritis in 1983, is a gram-negative, spiral microaerophilic, fastidious organism. Generally all patients with gastric ulcer have H. pylori and eradication of the bacteria is followed by the resolution of gastritis [Cover and Blaser, 1995; Blaser, 1996]. It is estimated that H. pylori infection increases the risk of gastric cancer by approximately six times. Epidemiological studies showed that about 50% of the world population is infected with H. pylori (80% and 40% of adults in developing and developed countries, respectively) but only part of the infected population develop clinical symptoms.

The unique characteristic of H. pylori infections is persistence of the agent within the gastric mucous. The immune response against the infection is not able to eradicate the infection [Dunn et al, 1997]. Histological examination shows that the bacteria are in close association with mucus layer and underneath gastric cells [Lee et al, 1993]. The microorganisms produce a number of adhesins which mediate attachment of the bacteria to cognate receptors present in gastric mucus and epithelium [Boren and Falk, 1995; Dunn et al, 1997]. They agglutinate erythrocytes and it has been shown that the ability to adhere to gastric epithelium correlates with its ability to agglutinate red blood cells. Adhesion to gastric epithelial cells and to the mucus layer coating such surfaces is considered to be the most important factor enabling the pathogen to cause persistent infection [Boren and Falk, 1995]. It is an object of the present invention therefore to provide anti-adhesion compounds for anti-adhesion therapy which can be an alternative to the conventional antibiotic treatment.

Bacterial activity of over 500 different bacteria have been implicated in both human dental plaque and caries (cavities). Adhesion of the bacteria to each other (intraspecies) and to other bacterial species (intergeneric coaggregation) as well as to oral surfaces is one of the major factors leading to dental plaque as well as carries and periodontal diseases.

It would be useful to have additional anti-aggregation medicaments for use in oral hygiene. U.S. Pat. No. 5,362, 480, columns 1–3 provides a discussion on bacterial adhesions and oral hygiene. Ofek and Doyle, 1994 provides a general discussion of bacterial adhesion incorporated herein by reference in their entirety.

Briefly, microbial accumulations on the tooth surfaces, termed dental plaque, are the causative agents of both dental caries and periodontal diseases [Slots, 1977; Socransky et al., 1982; Savit and Socransky, 1984; Dzink et al., 1985, 1988]. The adhesion of bacteria to the pellicle-coated tooth surface appears to be the first step in the formation of dental plaque [Gibbons and van Houte, 1975; van Houte, 1980]. Oral streptococci and to some extent Actinomyces sp. are the prominent early colonizers of the tooth surfaces [Nyvad and Kilian, 1990] and apparently attach to macromolecules selectively adsorbed to tooth surfaces [Gibbons et al., 1991].

Microorganisms that progressively accumulate thereafter, mostly gram negative anaerobic bacteria, in the gingival crevice area, are the late colonizers and are believed to play a central role in the initiation and progression of periodontal diseases. In this second step the bacteria co-aggregate or adhere to each other. The primary constituents of dental plaque are bacteria in a matrix composed of extracellular bacterial polymers and salivary products. The bacterial species present in dental plaque are heterogeneous and they change progressively as the clinical condition goes from normal health through gingivitis to advanced stages of periodontitis [Moore and Moore 1994].

Studies in vitro of coaggregation among oral bacteria revealed that coaggregation is essentially the result of adhesion mediated by specific interactions between complementary molecules on the surfaces of the participating bacteria [Kolenbrander et al, 1993]. Several hundreds of oral bacterial pairs were found to participate in this type of multigeneric coaggregation reactions in vitro, but only for handful of pairs the molecular mechanisms have been characterized [Ofek and Doyle, 1994]. In many cases the coaggregation involves lectin-carbohydrate interaction whereby the sugar residues on one bacterial pair interact with a lectin on the surface of the other bacterial pair.

Based on the ability of simple and complex sugars to inhibit coaggregation, a number of distinct specificities are now recognized including lactose, sialic acid, rhamnose and fucose inhibitable coaggregations. It should be noted however, that still a large number of coaggregating pairs are not inhibited by any of the carbohydrates tested and therefore they may have a distinct specificity involving surface constituents other than lectin and carbohydrate [Ofek and Doyle, 1994].

It is therefore an object of the present invention to provide compounds to inhibit interbacterial coaggregation or adhesion of oral bacteria or to reverse existing coaggregation.

There is presently anecdotal and scientific evidence that cranberry juice or some fraction thereof inhibits or reduces bacterial infections of the bladder [Avorn et al, 1994], restricted to P-fimbriated bacteria. Currently, it is believed that this action is due to interruption of the adhesion of P-fimbriated bacteria to mammalian cells.

U.S. Pat. Nos. 5,002,759 and 5,362,480 disclose anti-adhesion compositions that can be used in treating oral bacteria. However, neither of these patents disclose compositions from Vaccinium, and in particular cranberry or blueberry, and are not the composition of the present invention.

U.S. Pat. No. 5,185,153 provides a composition for use in oral compositions for the lysis and killing of oral bacteria. The '153 patent does not derive the agent from cranberry and is not the composition of the present invention.

U.S. Pat. No. 5,474,774 to Walker et al issued Dec. 12, 1995 does disclose an extract from cranberry which is enriched for an activity which inhibits bacterial adhesion to surfaces. However, the extract is not the composition of the present invention as shown in comparative Example 5 herein below. Further, the method of the '774 patent initiates the extraction from whole cranberries with multiple extraction steps. PCT/US96/03978 (WO 96/30033) published application further discloses an extract/composition. However, as shown herein below the composition of PCT/US96/03978 is not the composition of the present invention as shown in comparative Example 5 herein below.

U.S. Pat. No. 4,857,327 to Virdalm discloses a preparation isolated from the remainder of the berries after the pulp flesh has been removed. In the art of juice making the material from the Virdalm '327 is referred to as the "press cake" which is not used for making juice. Juice is derived from the "pulp flesh". Therefore since the starting point for the Virdalm '327 product is from the remainder after discarding the pulp flesh and thereby the juice.

U.S. Pat. No. 5,683,678 to Heckert et al discloses an oral composition containing anthocyanins isolated from cranberries. However, the extract is not the composition of the present invention as shown in comparative Example 5 herein below.

It is an object of the present invention to use commercially prepared juice or concentrate from berries of the Vaccinium plant genus as the starting source of isolation with minimal extraction steps of an anti-coaggregation, adhesion fraction.

SUMMARY OF THE INVENTION

According to the present invention, a non-food composition comprising a suitable carrier and an effective amount of an aggregation/adhesion inhibitory fraction isolated from juice from berries of the Vaccinium plant genus is provided. In an embodiment the anti-aggregation fraction is isolated from cranberry juice. Further, the invention includes a method of inhibiting interbacterial adhesion including mucosal adhesion of *Helicobacter pylori*, coaggregation of oral bacteria, and reversing adhesion of oral bacteria by treating with the isolated fraction from cranberry juice and a pharmaceutically acceptable carrier.

The anti-aggregation/adhesion water extract fraction is characterized as being polymeric and having a molecular weight $\geq 14,000$; an elemental analysis of carbon 43–51%, hydrogen 4–5%, no nitrogen, no sulfur and no chlorine; an NMR line spectrum as set forth in FIGS. 2A and 2B; and an ultraviolet spectrum with an absorption peak at 280 nm in neutral or acidic pH solution which is absent in alkali solutions. This fraction exhibits adhesion inhibitory activity against P fimbriated bacteria, oral bacteria as well as reversal of aggregation/adhesion of oral bacteria and adhesion inhibitory activity against *Helicobacter pylori*.

The present invention further provides two methods of extracting the composition of the present invention.

BRIEF DESCRIPTION OF THE DRAWINGS

Other advantages of the present invention will be readily appreciated as the same becomes better understood by reference to the following detailed description when considered in connection with the accompanying drawings wherein:

FIG. 9 is a graph showing the inhibition by NDM of adhesion of *H. pylori* to human gastric musin. Human mucin (0.1 ml, 1 mg/ml protein in saline) was immobilized on the bottom of microtiter plates and exposed to Helicobacter suspension in PBS or PBS containing 0.1 mg/ml NDM. After washing off non bound bacteria, the amount of mucin-adherent bacteria was quantitated by monitoring the urease activity of these bacteria over time, as determined by calorimetric assay of urea hydrolysis at OD 660.

DETAILED DESCRIPTION OF THE INVENTION

The present invention provides a non-food composition comprising a suitable carrier and an effective amount of the isolated adhesion inhibitory water extract fraction from juice isolated from the pulp flesh of berries of the plant genus Vaccinium as the active ingredient for use in oral hygiene and as a gastro-intestinal/enteric therapeutic. In one embodiment the isolated adhesion inhibitory fraction is designated as PF-1 and is characterized by:

being a polymeric compound having a molecular weight $\geq 14,000$; and exhibiting adhesion inhibitory activity against oral bacteria, H. pylori, and including coaggregation inhibition and reversal of coaggregation.

Figure 2A:
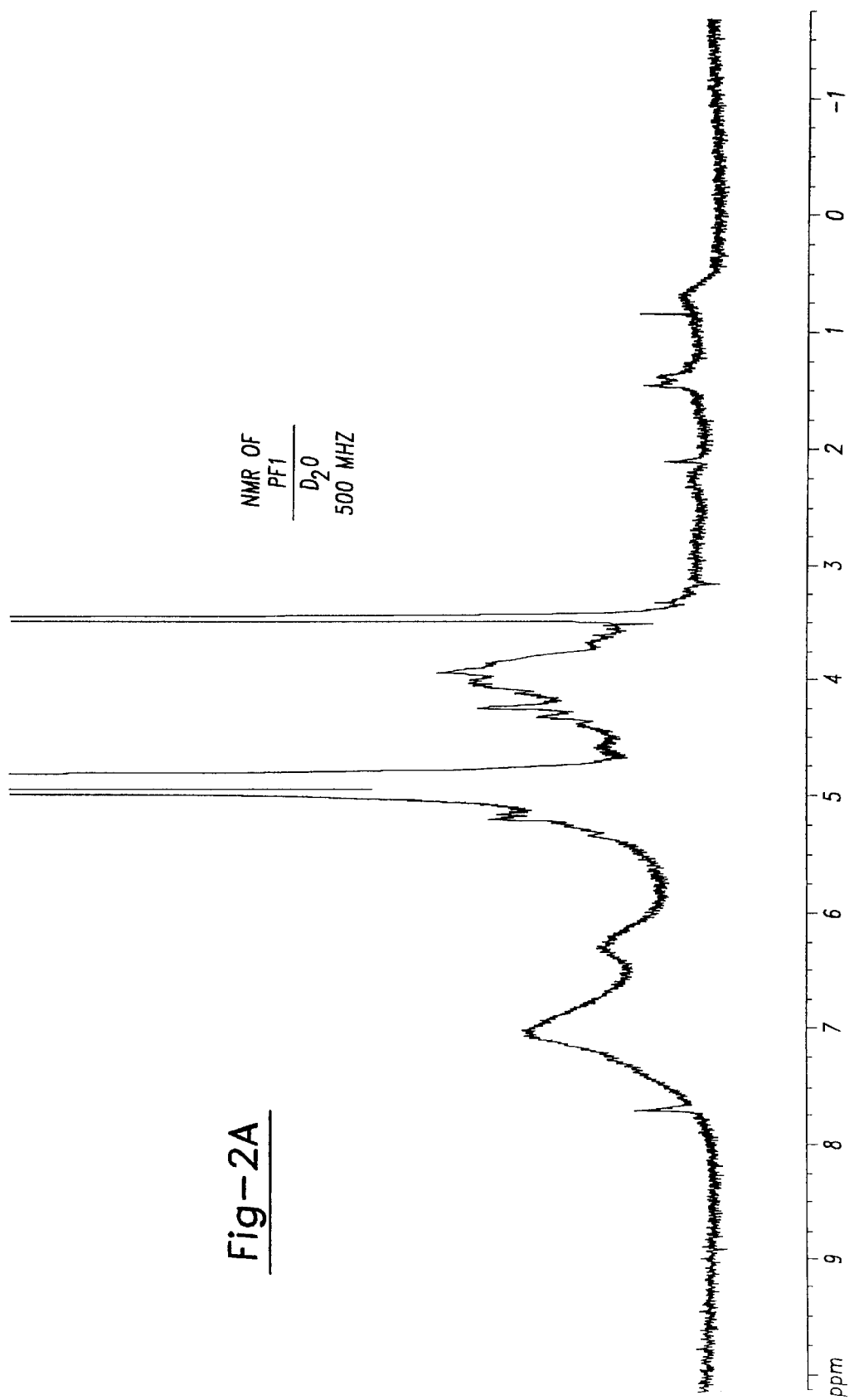
FIG. 2A–2C are NMR line spectra of the adhesion-inhibitory active fraction from cranberry juice, wherein (A) is PF-1 (proton NMR), (B) is PF-1 after removal of bound iron (proton NMR), and (C) is acid-hydrolysis product (carbon NMR)
Figure 2B:
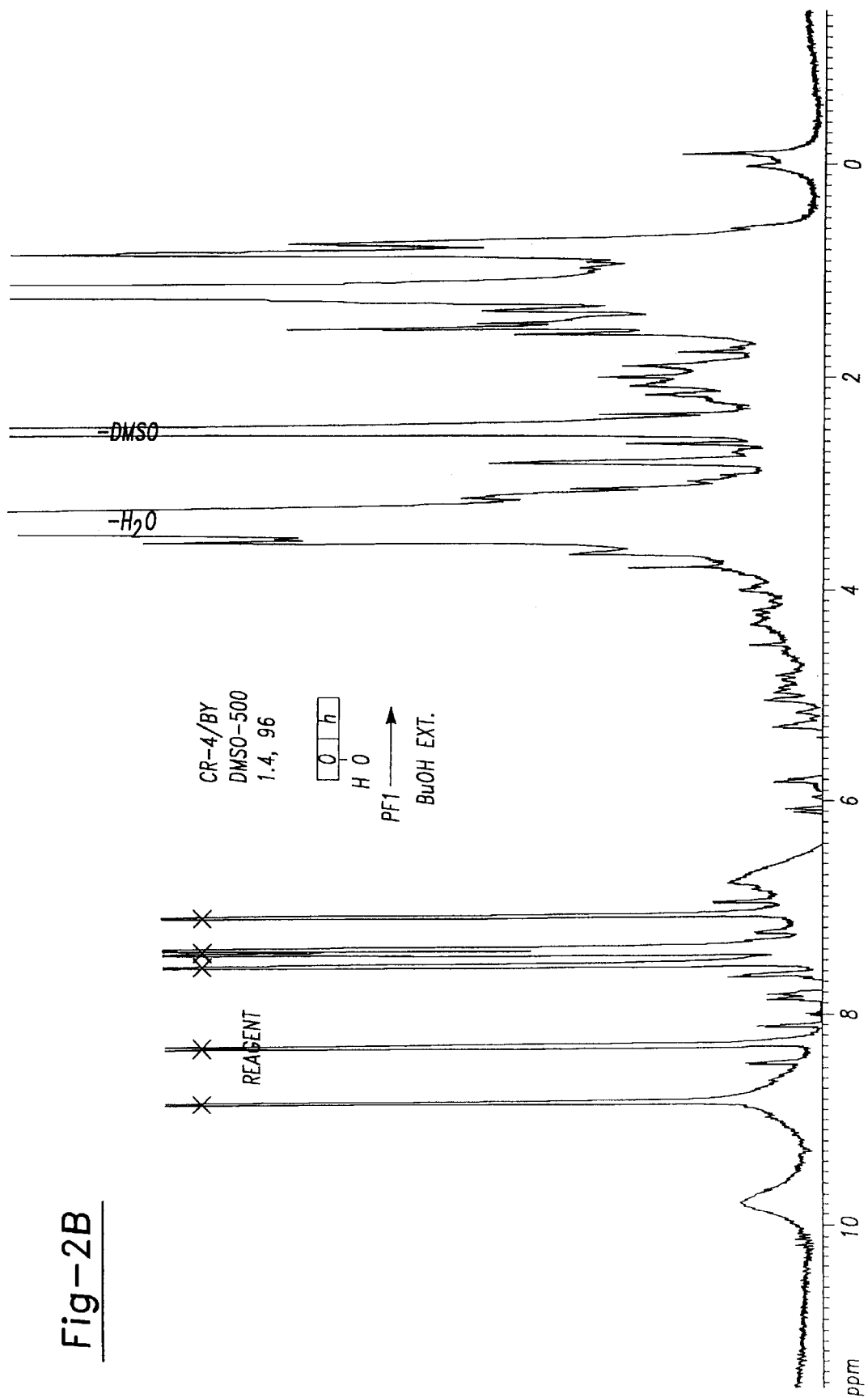

The active fraction is further characterized as:

having an elemental analysis of carbon 43–51%, hydrogen 4–5%, no nitrogen, no sulfur and no chlorine;

having a characterizing NMR line spectrum as set forth in FIGS. 2A and 2B;

having an ultraviolet spectrum with an absorption peak at 280 nm in neutral or acidic pH solution which is absent in alkali solutions; and exhibiting microbial-adhesion-inhibitory activity.

The composition of the present invention can be administered to a patient in need of such a composition for treating *H. pylori* infections (see Example 9 and 10 herein) as an active ingredient and a pharmaceutically acceptable carrier or diluent as well as for oral hygiene. Generally, the concentration of the isolated adhesion inhibitory fraction is between 1 μg and 10 mg per milliliter.

In a preferred embodiment the fraction is prepared from cranberry juice or juice concentrate. However, other species of the plant genus Vaccinium can be used in the practice of the present invention such as, but not limited to, bilberry and blueberries [Ofek et al, 1993, page 198, Table 2].

Oral hygiene refers to the control of dental plaque, dental caries and periodontal disease (gingivitis and periodontitis).

Anti-*H. pylori* therapeutic refers to the control of *H. pylori* gastric infection by anti-adhesion compounds for anti-adhesion therapy. It further refers to the inhibition of adhesion of *H. pylori* to human mucin as shown herein in the Examples.

Adhesion refers to the general aggregation of bacteria to each other, to other cell surfaces and to non cell surfaces generally through adhesion molecules on the surface of the bacteria. Further as used herein coaggregation refers to the aggregation/adhesion of two or more bacteria, including bacteria of different species, and coaggregation reversal refers to reversing the aggregation or adhesion (FIG. 4) between the bacteria. Inhibition of coaggregation or adhesion generally refers to prevention of the initial adhesion or aggregation of the bacteria. In general, anti-aggregation is used to refer to either or both inhibition and reversal of coaggregation, both intra- and inter-bacterial species, as indicated by the context of the use.

Coaggregation inhibition as used herein with reference to oral bacteria will have the in vivo effect of (i) prevention of accretion of new organisms to the already formed aggregates in the dental plaque and (ii) preventing the re-accumulation and recolonization of bacteria that have been just removed by the tooth brush or other means allowing elimination from the oral cavity by the salivary flow/rinsing. If not prevented they can reattach to the clean tooth surface and/or the remaining dental plaque.

Reversal of coaggregation as used herein with reference to oral bacteria will have the in vivo effect of actively disrupting/dislodging or dispersing the existing dental plaque both on the tooth surface and on the mucosal surfaces.

Coaggregation inhibition and reversal of coaggregation as used herein with reference to *H. pylori* will have the in vivo effect of (i) prevention of accretion of new organisms to the already formed aggregates and (ii) preventing the re-accumulation and recolonization of bacteria on the mucosal surfaces and (iii) interruption of the adhesion of the bacteria with mucus layer and underneath gastric cells and interruption of their adhesins which mediate attachment of the bacteria to cognate receptors present in gastric mucus and epithelium.

P-fimbrial adhesion molecules bind specifically to a group of receptors identified as P-blood group antigens. The receptor(s) are present on the surface of various types of human cells—among other—urinary tract epithelium and red blood cells, and mediates attachment of the bacteria and subsequent colonization of the epithelium of the urinary tract. P-fimbriated *E. coli* cause agglutination (HA) of human red blood cells (RBC) [Ofek and Doyle; 1994].

The isolated adhesion inhibitory fraction PF-1 is insoluble in butanol and ethylacetate and is acid precipitable. It can be redissolved in water without loss of activity. The fraction loses partial activity upon heating in acidic solutions. It has a positive reaction in a phenol-sulfuric acid test as described in the Examples set forth herein below.

The present invention provides a method of inhibiting and reversing intergeneric coaggregation/adhesion of bacteria by treating with PF-1 (or PF-2 or NDM), and a pharmaceutically acceptable carrier. The concentration of PF-1, in the carrier is between 1 $\mu$g/ml and 10 mg/ml with a preferred embodiment between 10 $\mu$g/ml and 250 $\mu$g/ml. For inhibition of coaggregation a range between 10 $\mu$g/ml and 100 $\mu$g/ml has been shown to be effective. For reversal of coaggregation a range between 100 $\mu$g/ml and 250 $\mu$g/ml has been shown to be effective. For NDM the equivalent PF-1 units contained in the preparation are determined and the concentration adjusted accordingly. For PF-2, the PF-1 comparative unit is determined and the concentration adjusted accordingly (See Table 8).

In the method of treating oral bacteria the inventive compositions may constitute an integral part of a toothpaste, dental cream or gel, tooth powder, or mouthwash and applied during the regular brushing, or the compositions may be formulated and packaged as a separate treatment and applied separately before, after, and/or in between regular brushing times. The compositions may be applied by brushing, rinsing, chewing, and with active oral irrigation systems and any other means known in the art. Further chewing gums and lozenges as are known in the art may be used.

In the method of treating *H. pylori* infection in patients with such infections or with other bacterial infections that would benefit from the composition, the anti-adhesion fraction, PF-1, PF-2 or NMD, can be administered in various ways suitable for gastro-intestinal therapy. It should be noted that it can be administered as the compound or as pharmaceutically acceptable salt and can be administered alone or as an active ingredient in combination with pharmaceutically acceptable carriers, diluents, adjuvants and vehicles. The composition will generally be administered orally. Conventional methods such as administering the compounds in tablets, suspensions, solutions, emulsions, capsules, powders, syrups and the like are usable. Known techniques which deliver the anti-adhesion composition orally or intravenously and retain the biological activity are preferred.

Formulations that can be administered subcutaneously, topically or parenterally or intrathecal and infusion techniques are also comtemplated by the present invetnion as well as suppositories and implants. The pharmaceutically accetable carriers, diluents, adjuvants and vehicles as well as implant carriers generally refere to inert, non-toxic solid or liquid fillers, diluents or encapsulating material not reacting with the active ingredients of the invention. The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

Figure 1:
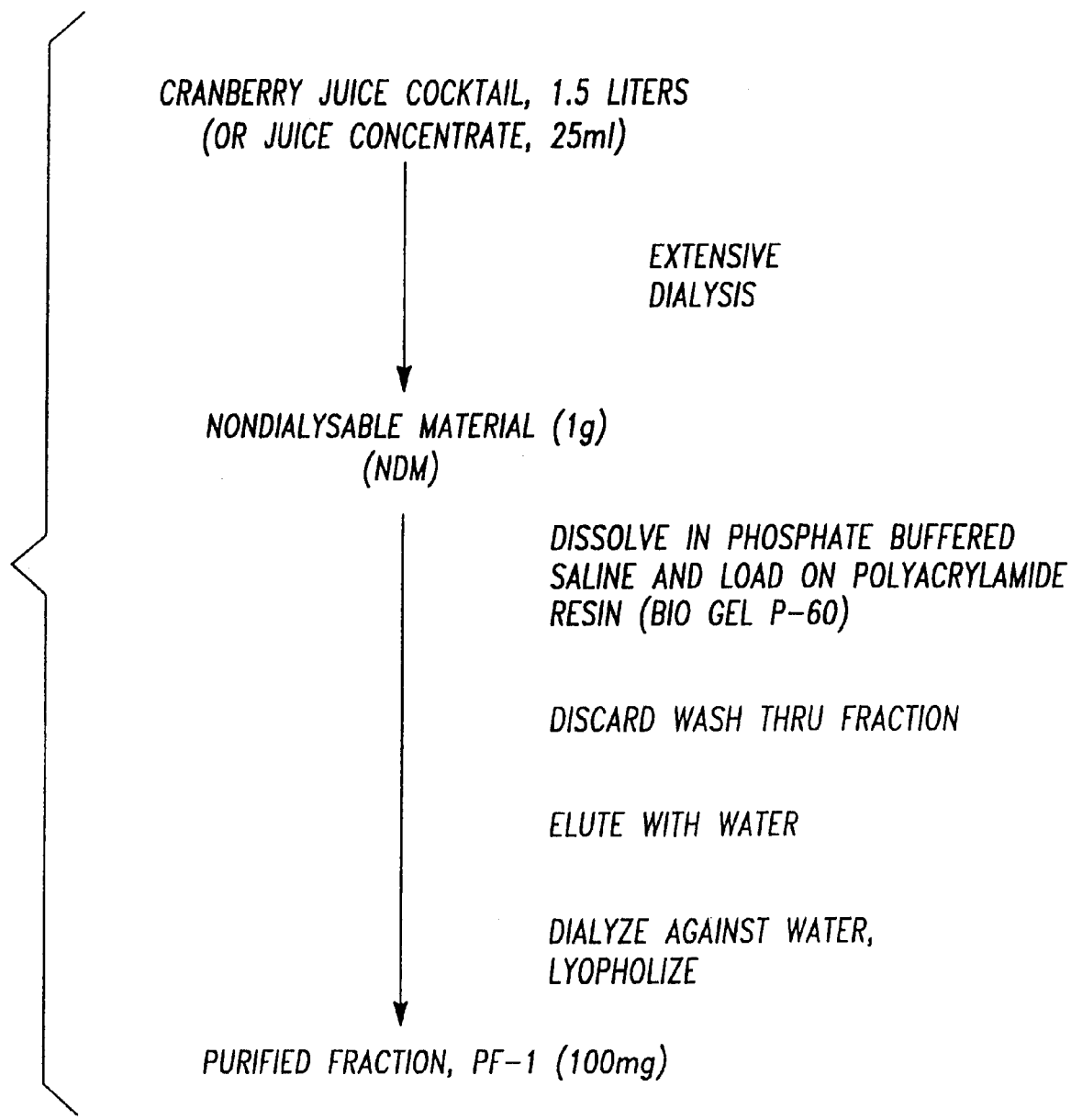
FIG. 1 is a schematic diagram of the isolation of the adhesion-inhibitory active fraction from cranberry juice wherein the starting amount is 1.5 liters of cranberry juice cocktail or 25 ml of concentrated cranberry juice.

In Example 1 set forth herein below, a method of isolating a fraction from cranberry juice, as the exemplar species of Vaccinium, exhibiting adhesion inhibitory activity against P fimbriated bacteria and oral bacteria is described. The method includes the steps of dialyzing cranberry juice, or a juice concentrate, extensively against double distilled water using dialysis tubing with a 12,000–14,000 molecular weight cut-off. The non-dialyzable material (NDM) remaining in the dialysis tubing is then lyophilized. The lyophilized NDM is then fractionated on a polyacrylamide resin column and the active fraction is eluted from the column with water, lyophilized, and designated PF-1 as shown in FIG. 1. In the Examples herein either the NDM or PF-1 fractions are used as indicated.

Further, in Example 8, additional preparation/purification steps are provided. When eluting the resin column 0.1 M ammonia can be used. Applicants have determined that some batchs of resin provide better yields when eluted with ammonia than water as is known in the art.

NDM as shown in the examples can be used in the present invention to inhibit or reverse intergeneric coaggregation/adhesion of oral bacteria, and a pharmaceutically acceptable carrier. The concentration of NDM however in the carrier is between 25 $\mu$g/ml and 100 mg/ml. For inhibition of coaggregation a range between 0.05 mg/ml and 0.4 mg/ml can be used. For reversal of coaggregation a range between 1 mg/ml and 4 mg/ml can be used.

The present invention also provides for an antibody directed against the isolated adhesion inhibitory fraction, PF-1, from cranberry juice. The antibody can be either polyclonal or monoclonal.

The antibodies are prepared against the isolated PF-1 (or portions of PF-1 that may be isolated as well as from NDM and PF-2) used as the immunogen. The material can be used to produce antibodies by standard antibody production technology well known to those skilled in the art, as described generally in Harlow and Lane, *Antibodies: A Laboratory Manual,* Cold Spring Harbor Laboratory, Cold Spring Harbor, N.Y., 1988 and Borrebaeck, *Antibody Engineering—A Practical Guide,* W. H. Freeman and Co., 1992.

For producing polyclonal antibodies, a host, such as a rabbit or goat, is immunized with PF-1, generally with an adjuvant and, if necessary, coupled to a carrier; antibodies to PF-1 are collected from the sera. More particularly, antibodies against PF-1 were prepared in rabbits by inoculation with mixtures containing formalin-killed bacteria of *E. coli* P-fimbriated (strain IHE-1002; in some reports strain is designated IHE or IHI) and PF-1. The mixtures are incubated for 1 hour at 37° C. to allow bacteria to absorb the substance. Immunization was carried out by intravenous injections of the mixtures containing increasing concentrations of bacteria and PF-1 ($10^8$–$10^9$ bacteria and 0.25–5 mg/ml of PF-1/injection) three times a week, for four weeks. Two weeks after the last injection, the serum is collected and analyzed by ELISA.

For producing monoclonal antibodies, the technique involves hyperimmunization of an appropriate donor with the PF-1 as above, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice,* Blackwell Scientific Publications, Oxford, 1982.) The binding of antibodies to a solid support substrate is also well known in the art. (see for a general discussion Harlow & Lane *Antibodies: A Laboratory Manual,* Cold Spring Harbor Laboratory Publications, New York, 1988 and Borrebaeck, *Antibody Engineering—A Practical Guide,* W. H. Freeman and Co., 1992) The detectable moieties contemplated with the present invention can include, but are not limited to, fluorescent, metallic, enzymatic and radioactive markers such as biotin, gold, ferritin, alkaline phosphatase, $\beta$-galactosidase, peroxidase, urease, fluorescein, rhodamine, tritium, $^{14}$C and iodination.

ELISAs are immunoassays which can be employed to identify and titer the anti-PF-1 antibody as well as the amount of PF-1 in a preparation. ELISA assays are well known to those skilled in the art. Both polyclonal and monoclonal antibodies can be assayed with an ELISA. Where appropriate other immunoassays, such as radioimmunoassays (RIA) and immunoblots, can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, Molecular Cloning: A Laboratory Manual, Cold Springs Harbor, N.Y., 1989.

The present invention provides for a composition comprising an effect amount of an isolated adhesion inhibitory fraction from Vaccinium, in a preferred embodiment the isolated adhesion inhibitory fraction from cranberry juice, PF-1, and a pharmaceutically acceptable carrier which does not react with the active ingredients of the invention and which does not decrease the biological activity of the present invention.

The composition is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is determined by such considerations as are known in the art. The amount must be effective to achieve improvement including but not limited to inhibition and/or reversal of oral intra- and inter-bacterial species coaggregation as described in the Examples herein below and to improvement or elimination of symptoms and other indicators as are selected as appropriate measures by those skilled in the art.

The present invention provides a non-food composition which comprises a suitable carrier and an isolated adhesion inhibitory fraction from Vaccinium. In a preferred embodiment an effective amount of the isolated adhesion inhibitory fraction PF-1 is used. However, in an alternative embodiment NDM can be used.

The preferred oral hygiene compositions of the present invention are in the form of toothpaste (dental cream, gel or tooth powder), as well as mouthwash, pre-brushing, or post-brushing rinse formulations, chewing gums and lozenges.

Ingredients typically included in toothpastes and gels may be used in toothpaste and gel compositions in accordance with the invention as are known in the art. Suitable ingredients include abrasive polishing materials, sudsing agents, flavoring agents, humectants, binders, sweetening agents, and water and are described generally herein below.

Mouthwashes are typically comprised of a water/alcohol solution, flavor, humectant, sweetener, foaming agent, and colorant.

Abrasives which may be used in the compositions of the invention include alumina and hydrates thereof, such as alpha alumina trihydrate, magnesium trisilicate, magnesium carbonate, aluminosilicates, such as calcined aluminum silicate and aluminum silicate, calcium carbonate, zirconium silicate, polymethyl methacrylate, powered polyethylene, silica xerogels, hydrogels and aerogels and the like. Also, suitable as abrasive agents are calcium pyrophosphate, insoluble sodium metaphosphate, calcium carbonate, dicalcium orthophosphate, particulate hydroxyapatite and the like. Depending on the form which the oral composition is to take, the abrasive may be present in an amount of from 0 to 70% by weight, preferably 1 to 70% by weight, more preferably from 10 to 70% by weight, particularly for toothpastes.

Humectants contemplated for use in the present invention include glycerol, polyol, sorbitol, polyethylene glycols, propylene glycol, hydrogenated partially hydrolyzed polysaccharides and the like. The humectants are generally present in amounts of from 0 to 80%, preferably 5 to 70% by weight, particularly for toothpastes. Thickeners may be present in toothpaste creams and gels at 0.1 to 20% by weight.

Binders suitable for use in the compositions of the invention include hydroxyethyl cellulose (Natrosol®), sodium carboxymethyl cellulose and hydroxypropyl cellulose (Klucel®), as well as xanthan gums, Irish moss and gum tragacanth. Binders may be present in the toothpaste of the invention to the extent of from 0.01 to 10%.

Suitable foaming agents include soap, anionic, cationic, nonionic, amphoteric and/or zwitterionic surfactants. These may be present at levels of 0 to 15%, preferably 0.1 to 15%, more preferably 0.25 to 10% by weight.

Certain pyrophosphate and other polyphosphate salts have been disclosed in U.S. Pat. Nos. 4,515,772 and 4,627,977 as being useful as anti-calculus agents. These include di- and tetra-alkali metal pyrophosphates wherein the alkali metals are preferably selected from the group consisting of sodium and potassium. Polyphosphate salts may be included generally in the amount such that it provides for at least 0.5% polyphosphate anions, the upper level being about 10%, preferably about 7.5%.

Various anionic polymers may be employed as anticalculus and/or antiplaque agents. Suitable polymers include carboxylate polymers, sulfonate polymers, polymers containing a sulfonate and a carboxylate moiety, carboxylate polymers containing phosphinate units, and mixtures thereof. Some carboxylate polymers suitable in the present compositions are described by Gaffar et al., U.S. Pat. No. 4,808,400, incorporated by reference herein. Other carboxylate polymers containing mono- or disubstituted hypophosphite units along the polymer backbone are described in a U.S. Pat. No. 5,011,682 incorporated by reference herein. The anionic polymers may be included at a level from about 0.01 to about 10%, preferably from about 0.05 to about 5.

Zinc salts are disclosed as anti-calculus and anti-plaque agents in U.S. Pat. No. 4,100,269 and in U.S. Pat. Nos. 4,416,867, 4,425,325 and 4,339,432. Preferred compositions of the invention include zinc salts, particularly zinc citrate. The zinc compounds may be present in the compositions in amounts sufficient to furnish about 0.01% to about 4% zinc, or preferably about 0.05% to about 1%, zinc ion.

Fluoride sources used in toothpastes such as sodium fluoride, stannous fluoride, sodium monofluorophosphate, zinc ammonium fluoride, tin ammonium fluoride, calcium fluoride and cobalt ammonium fluoride may be, and preferably are, included for delivering anti-caries benefit. Preferred compositions of the invention include the fluoride source. Fluoride ions are typically provided at a level of from 0 to 1500 ppm, preferably 50 to 1500 ppm, although higher levels up to about 3000 ppm can be used.

Sweeteners suitable for use in the present dentifrice, preferably at levels of about 0.1% to 5%, may include saccharin and other non-caloric sweeteners as known in the art. Flavors are usually included in toothpastes in low amounts, such as from 0.01 to about 5% by weight, especially from 0.1% to 5%. Titanium dioxide is a suitable whitener but others known in the art may be used. Dyes/colorants suitable for dentifrices, i.e., FD&C Blue #1, FD&C Yellow #10, FD&C Red #40, etc., can be employed in the dentifrices of the invention or others known in the art.

Water-soluble antibacterial agents, such as chlorhexidine digluconate, hexetidine, alexidine, quaternary ammonium anti-bacterial compounds and water-soluble sources of certain metal ions such as zinc, copper, silver and stannous (e.g., zinc, copper and stannous chloride, and silver nitrate) can also be included.

Various other optional ingredients may be included in the compositions of the invention, such as preservatives, vitamins such as vitamin C and E, other anti-plaque agents such as stannous salts, copper salts, strontium salts and magnesium salts. Also included may be pH adjusting agents, anti-caries agents such as urea, calcium glycerophosphate, sodium trimetaphosphate, silicone polymers, plant extracts, desensitizing agents for sensitive teeth such as potassium nitrate and potassium citrate, and mixtures thereof.

Casein and/or its hydrolysate may be included as anticaries agents, e.g. at a level of 0.01 to 20% by weight, preferably 0.1 to 10%.

The corresponding compounds mentioned above which are used in toothpastes, are generally suitable within the ranges above for mouthwashes as well. The mouthwash can include ethanol at a level of from 0 to 60%, preferably from 5 to 30% by weight.

The present invention also provides for a fortified food composition for oral hygiene comprising a suitable food carrier and an effective amount of an isolated adhesion inhibitory fraction from Vaccinium. In a preferred embodiment the food carrier is a fruit juice and the isolated adhesion inhibitory fraction is PF-1. The food carrier is selected such that it does not decrease the biological activity of the present invention. The concentration of the adhesion inhibitory fraction in the food carrier is between 10 $\mu$g/ml and 10 mg/ml or the equivalent weight/volume concentration for non-liquid foods.

Figure 6:
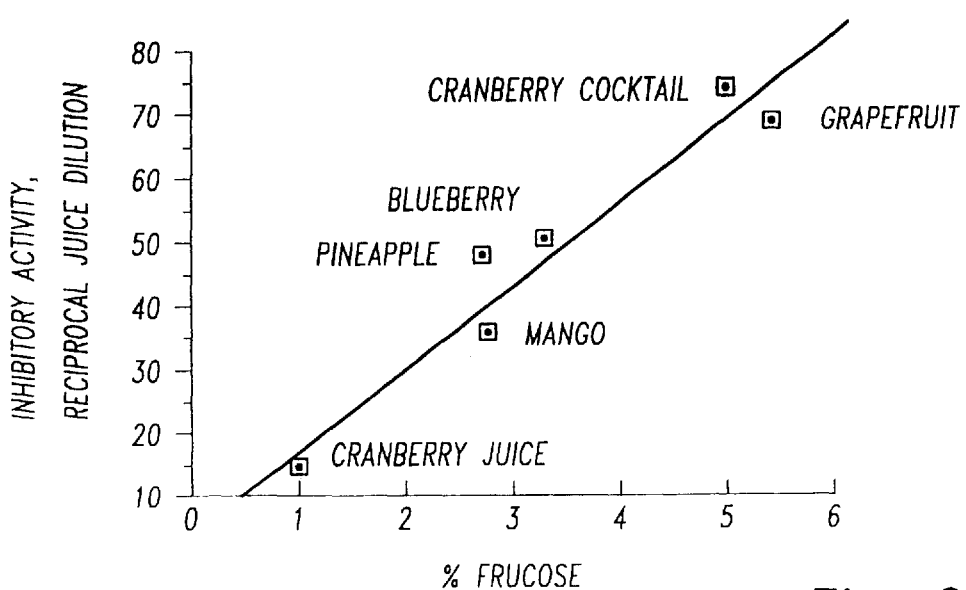
FIG. 6 is a graph of prior art results showing correlation between inhibitory activity against type 1 fimbrial adhesion of *E. coli* and fructose content of various juices.

The ability of cranberry products to inhibit *E. coli* adhesion to surfaces such as bladder cells was shown as early as 1984 by Sobota [Sobota, 1984; Schmidt and Sobota, 1988]. Applicants have confirmed these results with Ocean Spray cranberry juice cocktail [Zafriri et al, 1989; Ofek et al, 1991; Ofek et al, 1993]. Applicants confirmed that fructose inhibits adhesion of *E. coli* mediated by type 1 fimbriae (FIG. 6 [Ofek et al., 1993].

An inhibitor, PF-1, was also found that is a polymeric substance which inhibits mannose resistant adhesion of urinary isolates of *E. coli* to surfaces such as human erythrocytes. The specificity of adhesion of some of these isolates was mediated by P fimbriae. PF-1 has, however, no effect on adhesion of diarrhoeal isolates of *E. coli*.

The specificity of *E. coli* adhesion is different from that of the oral bacteria [Ofek and Doyle, 1994; Offek, 1996]. For example, many of the characterized oral adhesins are resistant to mannose while being sensitive to galactose or other carbohydrates. Hence, it is impossible to infer from the inhibition studies performed with *E. coli*, the behavior of the cranberry preparation in tests which include oral bacteria. It was therefore unexpected to find that PF-1 had activity against oral bacteria.

In initial work, PF-1 was tested for its ability to inhibit (by addition of the PF-1 preparation to one of the bacterial pairs before mixing with the other) or to reverse (by its addition to performed coaggregates) the coaggregation of selected bacterial pairs including members of the following bacterial species: *Gemella morbillorum; Streptococcus oralis; Streptococcus sanguis; Actinomyces israelii, Actinomyces naeslundii; Capnocytophaga ochracea, Capnocytophaga sputigena; Prevotella intermedius, Porphiromonas gingivalis; Fusobacterium nucleatum* and *Actinobacillus actinomycetemcomitans*. For most of the pairs, the lowest concentration of PF-1 needed for inhibition was in the range of 50 to 10 μg/ml, whereas for reversal of coaggregation it was in the range of 125 to 200 μg/ml. Coaggregation of several pairs (e.g. *F. nucleatum* and *A. naeslundii*) was reversed by the cranberry PF-1 although they were resistant to all carbohydrates tested. The juice-derived material did not reverse the coaggregation of a number of pairs tested including members of Streptococcus, Fusobacteria, Capnocytophaga and Actinomyces, which indicates the specificity of the inhibitor.

As shown in Table 4, more extensive testing with non dialyzable material (NDM) from cranberry (which contains PF-1) showed the same pattern. Of a total of 37 bacterial pairs tested, 29 (78.1%) pairs showed reversal of intergeneric oral bacterial adhesion (coaggregation) by the NDM. The NDM was used at a concentration of s2500 μg/ml. Thirteen (36%) did not have the coaggregation reversed.

The above discussion provides a factual basis for the preparation and method of use of an isolated adhesion inhibitory fraction from cranberry juice. The methods used with and the utility of the present invention can be shown by the following non-limiting examples and accompanying figures.

EXAMPLES

General Methods:

Reagents: Cranberry juice as available commercially is used and cranberry concentrated material (CCM) obtained directly from Ocean Spray Cranberries Inc., Lackeville-Middleboro Mass. 02349 is used for the isolation of PF-1. Bacterial strains used are of human gingival crevice origin (P. Kolenbrander, NIDR, NIH). All bacteria were grown at 37° C. under anaerobic conditions (GasPack Anaerobic System, BBL) in Schaedler broth with the exception of *F. nucleatum* PK1594 which is grown either in Schaedler broth or brain heart infusion broth (BEL). Cells are harvested, washed with coaggregation buffer (CAB: 0.001 M Tris, 0.0001 M $CaCl_2$, 0.0001 M $MgCl_2$, 0.15 M NaCl, 0.02% $NaN_3$, adjusted to pH 8.0) and stored at 4° C. until used.

Figure 4:
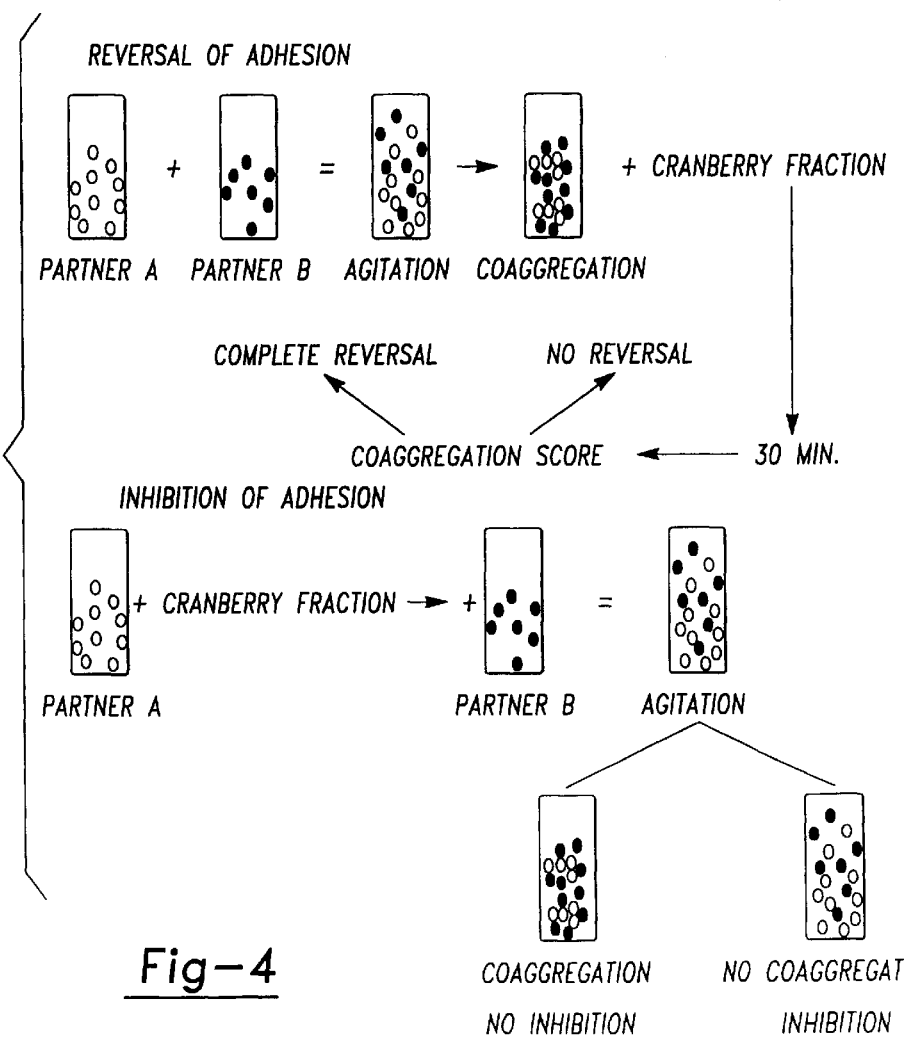
FIG. 4 is a schematic diagram of method to determine reversal of adhesion (coaggregation) and method to show inhibition of adhesion (coaggregation) of oral bacteria.
Figure 5:
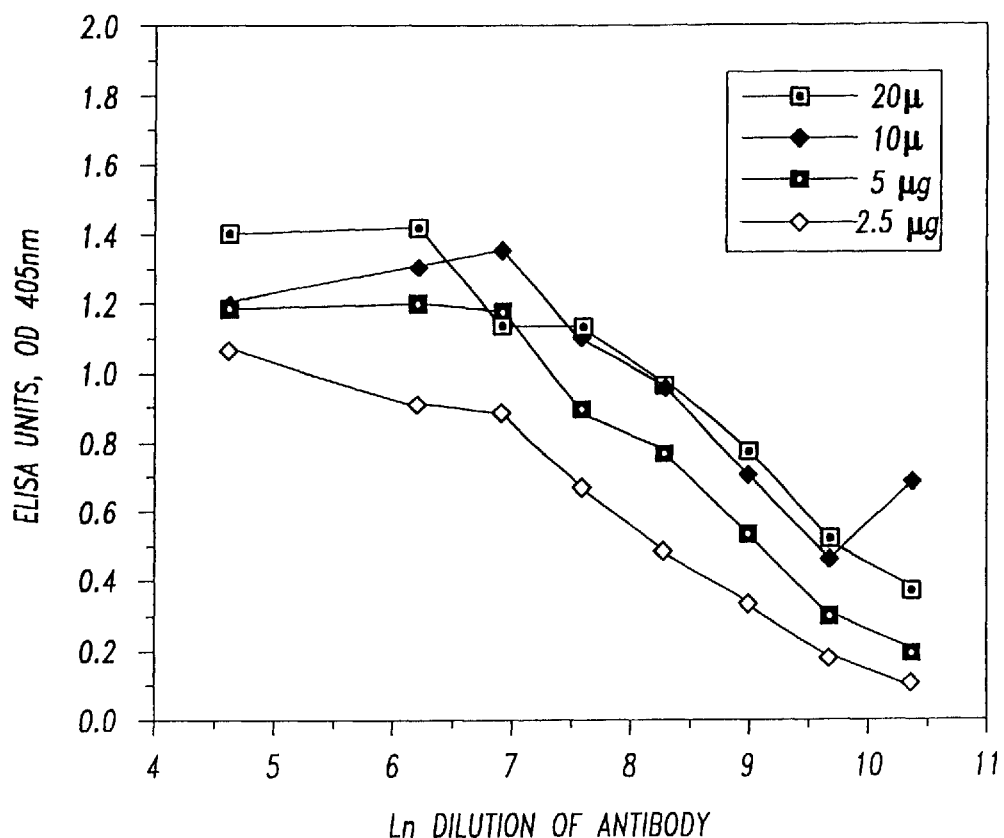
FIG. 5 is a graph showing the results from an ELISA titrating anti-PF-1 antibody.

Visual Coaggregation Assay [Kolenbrander, 1988; Kolenbrander et al, 1989; Kolenbrander et al, 1993; Weiss et al, 1987]: Cell suspensions are adjusted to optical density of 1.5 at 400 nm (UV-Vis Spectrophotometer, Shimadzu) corresponding to approximately $10^8$ cells/ml. The appropriate partners (see Table 4; FIG. 4) of 50 μl each are mixed together vigorously for 10 seconds. A visual rating scale of 0 to 4 is used to grade the reactions. 0=evenly turbid suspension with no visible aggregates indicating no coaggregation; 1=few coaggregates; 2=coaggregates formed remain in suspension; 3=aggregates form big clumps and precipitate out of solution but fluid remain opaque; and 4=maximal clumping leaving a clear supernatant.

Visual Coaggregation Assay to Screen Coaggregation Inhibitors:

Inhibition of coaggregation was assayed by pre-incubating 40 μl of either one of the two test bacterial species with 20 μl of serial dilutions of the cranberry fraction for 30 minutes followed by adding 40 μl of the other bacterial species. The coaggregation is scored as described above.

Reversal of coaggregation was assayed by incubating 40 μl of bacterial suspension of one species with 40 μl of bacteria of another species. The mixture is incubated for 30 minutes with constant agitation followed by adding 20 μl serial dilutions of cranberry fraction. After further incubation of 15 minutes, the coaggregation is scored.

Haemagglutination (HA): *E. coli* IHE expressing P-fimbriae, grown on TSA agar at 37° C. for 48 hours are harvested into PBS buffer and the bacterial suspension is two-fold serially diluted in 96 well (U-shaped) microtitration plates (50 μl/well). To each well 25 μl of 5% human erythrocyte (group A) suspension is distributed. After a 30 minute incubation at room temperature, the highest dilution of the bacterial suspension causing HA is determined so that the minimal HA unit is determined for use in testing samples.

To serial two-fold dilutions of samples (50 μl/well of microtitration plate), 50 μl of the bacterial suspension (6 minimal HA units) is added and the mixture is incubated at 37° C. HA is assayed on glass slides by mixing 50 μl of the sample-bacteria mixture from each well with 25 μl of 5% suspension of human group A erythrocytes. HA was recorded after 5 minutes at room temperature. HA inhibition (the highest dilution needed to complete inhibition of HA) is recorded according to control containing PBS instead of the tested sample.

Figure 3:
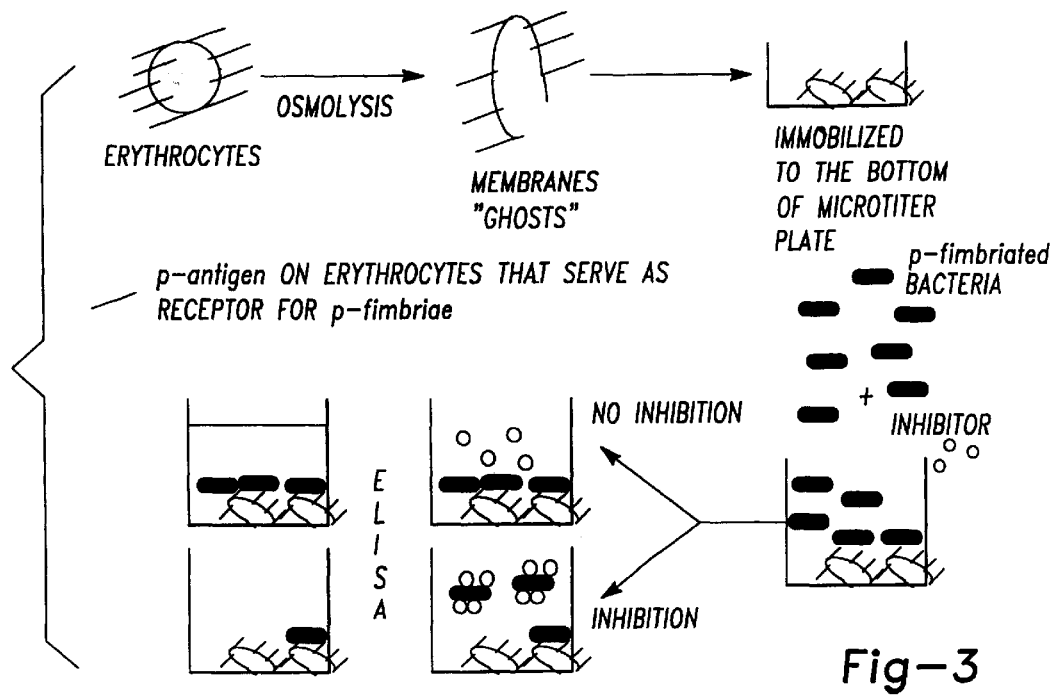
FIG. 3 is a schematic diagram of an ELISA to determine anti-adhesion activity of cranberry fractions against P-fimbriated bacteria.

ELISA for determination of adhesion inhibitory activity of cranberry fractions against P-fimbriated bacteria is as described in FIG. 3 and in Example 2 herein below.

NMR was undertaken using a Brucker AMX-360 and ARX-500 spectrometers.

Example 1

Isolation of PF-1

As an exemplar, the isolation of an anti-microbial adhesion inhibitory fraction (PF-1) from cranberry juice (cocktail or concentrate) was undertaken generally as diagramed in FIG. 1.

Isolation from Cranberry Juice Concentrate

Concentrated cranberry material (CCM; 500 ml), known as juice concentrate, is dialyzed against 5 liter distilled water (changed twice daily) for eight days. The commercial source was generally Ocean Spray, but other commercially available sources can be used. Dialysis tubing is from Spectrum Medical Industries, Inc., 60916 Terminal Annex, Los Angeles 90054. Applicants used Molecular cut off 12000–14000, diameter 28.6 cm (6.4 vol./cm; Catalog No. 132680).

The material remaining in the dialysis tube (non dialyzable material-NDM) is collected and lyophilized to powder, generally yielding 20 g. The NDM is used in some Examples as described herein. The NDM is solubilized with phosphate buffered saline (PBS) pH 7.5, 0.00 M Phosphate.

BioGel P-60 beads (BioRad; 16 gram pre-swelled with PBS for 2 days at room temperature) are used to build a column of 2.4×100 cm. The column is washed. The void volume of the column is 350 ml and the column is equilibrated with 750 ml PBS. Three grams of dry NDM is dissolved in 150 ml PBS and loaded on the column.

Colored material in NDM is bound by the beads. The column is washed exhaustively with PBS, which removes colored material and polysaccharides. Distilled water (750 ml) is then added and all material eluted is collected, dialyzed against distilled water and lyophilized. The material eluted is denoted as purified fraction 1 (PF-1). Generally about 300 mg dry weight PF-1 is obtained. It is stored at room temperature. In an alternative embodiment the material is eluted with ammonia (100 ml 0.1M) and the purified fraction denoted as PF-2 and dialyzed as for PF-1. As shown in Table 8, PF-2 performed in the assays similarly to PF-1, but there was a higher yield than PF-1, and PF-2 had a 2.5 to 5 fold increase as compared to NDM.

Isolation from Cranberry Juice Cocktail

The starting material was a commercially available cranberry juice or juice concentrate. The commercial source was generally Ocean Spray, but other commercially available juice sources can be used. The method is similar to the isolation from concentrate.

About 1.5 liters of the juice (or 25 ml of the concentrate) is dialyzed against double distilled water for 6 days at room temperature in dialysis tubing with a molecular weigh cutoff of 12,000 to 14,000. The dialysate is lyophilized and approximately, one gram of a nondialyzable material (NDM) is obtained.

The NDM is dissolved in 150 ml of PBS at pH 7.0, clarified by centrifugation and loaded onto a column (4×10 cm). A polyacrylamide resin is used, BioGel P-60.

The "wash-through" fraction with PBS (containing polysaccharides) is discarded and the active fraction is eluted from the column with water. This eluted aqueous, salt-free fraction is lyophilized yielding a reddish powder, PF-1. In general the yield of PF-1 is approximately 100 mg. When eluted with amonia the fraction is denoted as PF-2.

The isolates of PF-1 and/or PF-2 are standardized by their anti-adhesion/aggregation activity, utilizing hemagglutination assay, ELISA and the visual coaggregation assay.

Example 2

Analysis of Activity

Upon isolation the PF-1 fraction (and/or NDM, PF-2) is analyzed/quantitated for their anti-adhesion/aggregation activity, utilizing the hemagglutination assay, ELISA and the visual coaggregation assay allowing both a functional determination and an antigenic determination. These assays determine the minimal concentration of the fraction (dilution) needed of the material (fraction) to provide inhibition of P-fimbriated bacterial adhesion to human erythrocytes (HA) or coaggregation of the oral bacteria. Table 1 provides exemplar data. (see also Table 8).

Activity is also measured utilizing a quantitation of inhibition by use of a modified ELISA protocol (FIG. 3) as described herein below.

Materials

Microtitration plates (flat bottom, Costar); Human Erythrocytes "Koscielak Ghosts" prepared according to procedure described by D. J. Anstee & M. J. A. Tanner (1974). 3.5 ml. of material is obtained from 10 ml of packed erythrocytes, divided into aliquots and stored at −70° C. until use.

Bacteria: $E.$ $coli$ IHE expressing P-fimbriae, grown on TSA agar at 37° C. for 48 hours are harvested into PBS buffer and the concentration determined according to Optical Density (O.D.). The bacterial suspension is stored in aliquots at −20° C. until use.

Rabbit antiserum against $E.$ $coli$ IHE is prepared as described herein above. Anti-rabbit IgG antibody conjugated to Horseradish peroxidase, from donkey (Amersham). Substrate OPD tablets (Sigma). PBS-Phosphate Buffered Saline, Bovine Serum albumin (BSA), Methyl alcohol (analytic) $H_2O_2$.

Procedure

A. Determination of Bacterial Binding
1. Ghosts are distributed (100 $\mu$l) in microtiter plate wells and dried at 37° C. overnight. Concentrations are according to titration curve.
2. Blocking with BSA in PBS (200 $\mu$l/well) for 1 hour at 37° C. Washing 2× with PBS.
3. Binding of bacteria: Various concentrations of the bacterial suspension in BSA-PBS are distributed into the wells (100 $\mu$l/well) and incubated at 37° C. for 1 hour. Washing 5× with PBS (gently).
4. Fixation: Methanol (100 $\mu$l/well) added and incubated at room temperature for 10 minutes. Washing 1× with PBS.
5. Antiserum diluted according to titration curve, in BSA-PBS, according to titration, 100 $\mu$l/well, incubation at 37° C. for 30 minutes. Washing 5× with PBS.
6. Conjugated anti-rabbit IgG antibody diluted according to manufacturer's instruction, 100 $\mu$l/well, incubation at 37° C. for 30 minutes. Washing 5× with PBS.
7. Substrate: 1 tablet in 25 ml. buffer (according to manufacturer's instruction), containing 10 $\mu$l of 30% $H_2O_2$, 100 $\mu$l/well, incubation at 37° C. followed by 10–15 minutes at room temperature.

B. Titration of Inhibitor

Bacterial suspension in concentration according to titration curve, incubated (vol/vol) at 37° C. for 1 hour with various concentrations of a potential inhibitor (diluted in water) and the mixtures are distributed into the wells (100 $\mu$l/well), as described in step 3 of the procedure herein above.

Bacteria incubated with PBS instead of inhibitor serve as control.

Recording of the Results

O.D. values, read after subtraction of O.D. value of the antiserum control (all elements of the assay, except bacteria) are proportional logarithmically to the number of bacteria bound.

Percent of inhibition is calculated from the difference between the number of bacteria bound in the presence and in the absence of inhibitor.

The minimal concentration of the inhibitor causing 50% inhibition is calculated according to the linear regression analysis of the results. For procedure used for "translation" of the O.D. values into the number of the bacteria bound/ well, see Athamna and Ofek (1988).

Testing of the System

Titration of bacteria dried in microtiter plates, in various concentrations (in water) with various concentrations of antiserum (AS) was tested. For further experiments AS diluted 1:150 was used. The minimal number of bacteria that can be detected was $5 \times 10^4$/well. Determination of optimal concentration of the ghosts Ghosts in amounts: 100, 50, 20, 10, 5, and 2.5 $\mu$l in a final volume with water to 100 $\mu$l/well were dried overnight (see step 1 of the procedure). Bacterial suspension in initial concentration 1×1010 /ml (O.D. 1.5 of the suspension diluted 1:10) was serially diluted and incubated, as described in step 3 of the procedure.

The ELISA values were dependent on the amount of ghosts immobilized in the microtiter plates. The range of 10–50 $\mu$l was tested. The binding signal was low on ghosts 20 $\mu$l and lower on 10 $\mu$l/well; 50 $\mu$l was optimal.

Titration of Binding of the Bacteria to 50 $\mu$l Ghosts.

Figure 7:
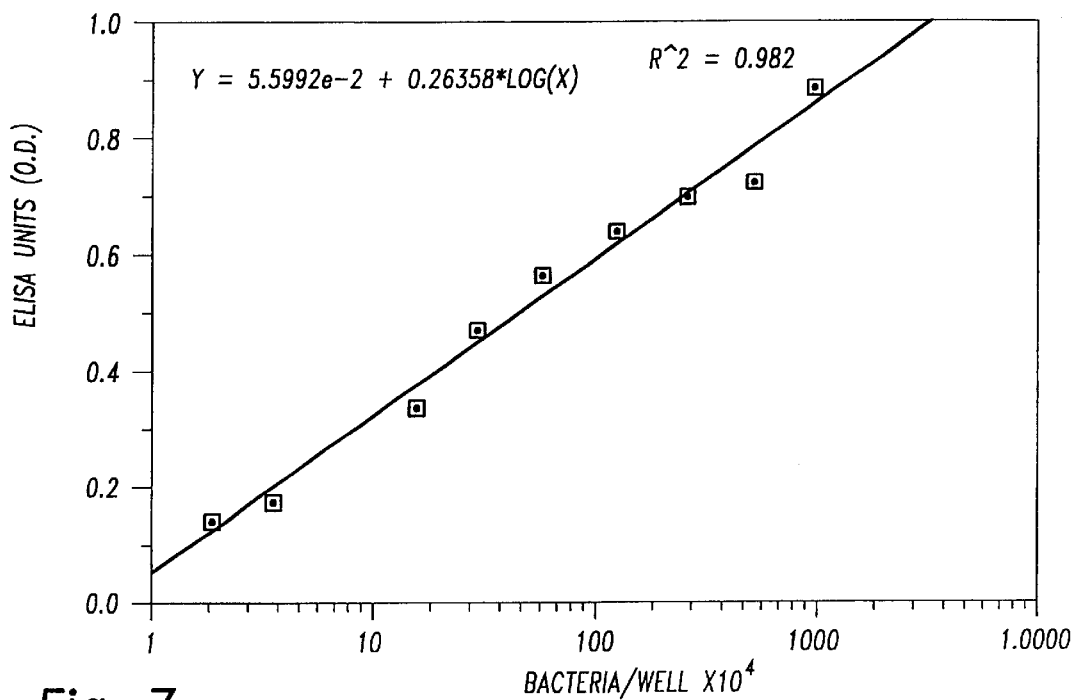
FIG. 7 is a standard curve to estimate number of bacteria per well from ELISA values.

Bacterial titration is shown in FIG. 7 where known amounts of bacteria were immobilized on the bottom of microtiter plates. ELISA is performed as described above and O.D. units can be plotted as a function of the log number of bacteria in each well. A linear regression curve including only values that increase proportionally to the number of bacteria can be used. Such a standard curve is then used to calculate the number of bacteria adherent to the erythrocyte ghosts, with and without treatment with PF-1 or other fractions, from the ELISA values obtained in the experiment.

Figure 8:
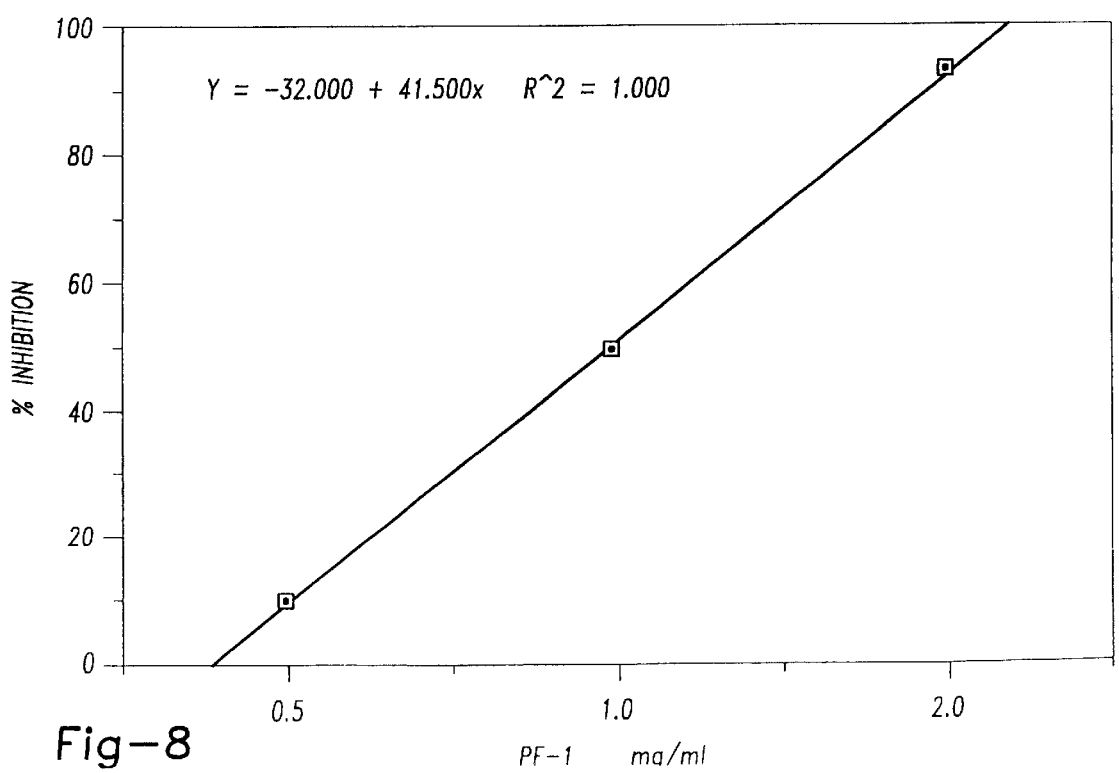
FIG. 8 is a graph showing the percent inhibition by PF-1 of adhesion of P-fimbriated *E. coli* to erythrocyte membranes (ghosts)

Inhibition of binding of bacteria with PF-1 2. According to FIG. 7, $5 \times 10^4$ to $5 \times 10^8$ bacteria can be detected. Optimal concentration of bacteria to be used in the test is $1 \times 10^8$/well. Applicants found that PF-1 inhibited binding of the P fimbriated bacteria in a dose related manner where 90–100% inhibition of binding was obtained with 2 mg/ml of PF-1 (FIG. 8). For greater sensitivity, the assay conditions are modified so that 50% inhibition can be achieved by lower concentrations of PF-1.

Example 3

Analysis of PF-1

PF-1 is acid precipitable in 2N HCl and can be redissolved in water without loss of activity. However, acid treatment (0.01 N HCl, 100° C., 30 minutes) results in reduced activity and not complete loss. It is not hydrolysed even in 2N HCl after 4 hours at 100° C.

Elemental analysis (Chemical Services, Organic Chemistry Department, Hebrew University of Jerusalem) of PF-1 after drying in vacuo at 60° C. gave the following range:

carbon 43–51% hydrogen 4–5%

No nitrogen, sulfur or chlorine

PF-1 gives a positive reaction in the phenol-sulfuric acid test [Dubois et al, 1956] suggesting the presence of carbohydrate of about 15% by weight using D-glucose as the standard.

Example 4

Further Analysis of PF-1

PF-1 was obtained as described in Example 1 and outlined in FIG. 1. It exhibited adhesion-inhibitory activity on P-fimbriated bacteria and oral bacteria down to a concentration of 10–25 $\mu$g/ml.

Previous attempts to analyze PF-1 by high resolution nuclear magnetic resonance (NMR) were unsuccessful due to severe line-broadening in the spectra (FIG. 2A). In an attempt to obtain interpretable spectrum, the following experiments were done.

One reason for the observed broadening could be the presence of bound iron. Attempts were, therefore, made to remove bound iron from PF-1. For this purpose PF-1 (100 mg/ml) was dissolved in 10% solution of methanol, 8-hydroxy quinoline (an iron chelating agent) was added (5 mg/ml) and the mixture was stirred for 3 hours at room temperature. The precipitate formed was removed by filtration or centrifugation and the methanol-aqueous solution was evaporated. The residue was dissolved in DMSO-d6 (10 mg/ 0.5 ml) and examined by NMR.

A sharp line spectrum was obtained (FIG. 2B). It shows that, as suspected, bound iron was masking the resolution of compounds in NMR. The iron free material was subject to acid metanolysis to obtain breakdown products of low molecular weight. The NMR spectrum of the products revealed that PF-1 contains inter alia phenyl rings (e.g. phenol rings), phenyl-CO groups, double bonds $CH_2$-chains and hydroxymethines and methylenes (FIG. 1C).

Further analysis of PF-1 (100 mg) was undertaken by extraction with butanol (10 ml) and then with ethylacetate (10 ml). No residues were found upon evaporation of the organic phases. Examination of dried material obtained from the aqueous phase by NMR gave a spectrum identical qualitatively and quantitatively with that of the starting material. These data demonstrate that PF-1 is devoid of any fraction soluble in the above organic solvents.

PF-1 was dissolved in 10% solution of methanol and loaded on Sephadex LH-20, P-10 or Dianion HP-20 columns. All of the material in PF-1 was adsorbed to the beads of the columns and could not be eluted with water.

PF-1 (50 mg) was acetylated by addition of pyridine (2ml) and acetic anhydride (2ml) followed by warm sonification for 2 hours. After incubation overnight at room temperature the solvents were evaporated to yield. poly-acetylated PF-1. The NMR spectrum of the product shows that the acetylation removed bound iron from some compounds, and the presence of acetyl groups (peaks around 2 ppm). While the nonacetylated starting material was retained in silica gel column, the acetylated product passed through the column, however, no single compound was obtained.

Acid methanolysis of PF-1 was performed by refluxing PF-1 (50 mg) in methanol (10 ml) and trifluoroacetic acid (2 ml) for 5 to 10 hours. The solvents were then removed by evaporation, the acid-methanolysed product was dissolved in 10% methanol solution and the iron removed as described above. The NMR spectrum of the iron free methanolysis product reveals sharp lines which denote saccharide like units, suggesting that acid methanolysis caused changes in the molecule. (See also Table 7 for anti-adhesion/aggregation activity of these fractions.)

Example 5

Comparative Analyses

As discussed herein above, U.S. Pat. No. 5,474,774 to Walker et al issued Dec. 12, 1995 does disclose an extract from cranberry which is enriched for an activity which inhibits bacterial adhesion to surfaces. Applicants have compared PF-1 to the material of the '774 patent with the following results.

As described in Example 3, PF-1 was dissolved in 10% solution of methanol in water and loaded on Sephadex LH-20, P-10 or Dianion HP-20 columns. All of the material in PF-1 adsorbed to the beads of either column and could not be eluted with water and water-methanol mixtures. The results suggest that the active material in PF-1 is different from that found in cranberry extracts described by '774 patent as shown in FIGS. 1 and 10 of the '774 patent and Table 1 of the '774 patent.

The adhesion inhibition compounds from cranberry fruit as described in '774 patent are low molecular weight, readily dissolved in organic solvents (FIGS. 1 and 10, '774 patent) as well as WO 96/30033. To examine whether such anti-adhesive compounds are present in cranberry juice, applicants employed a cranberry concentrated material (CCM; obtained from Ocean Spray) which contains both the high and low molecular weight compounds found in the cranberry juice.

Lyophilized CCM (100 mg) was extracted with butanol and ethylacetate as described for PF-1 (see Example 1 above). Most of the adhesion-inhibitory activity is retained in the aqueous phase. The NMR spectra of CCM fractions dissolved in the organic solvents and those retained in the aqueous phases were determined. Well resolved sharp peaks of various low molecular weight compounds are observed in the butanol and ethyl acetate fractions. These fractions lacked adhesion inhibitory activity (Table 2). Inhibition was tested as described previously (Zafriri et al, 1989) using P fimbriated *E. coli* and human erythrocytes as target cells for adhesion assays. For each fraction, listed in Tables 1 and 2 the concentration in μg/ml needed to inhibit hemagglutination of guinea pig erythrocytes caused by P-fimbriated *E. coli* and inhibition of coaggregation of oral bacteria was determined. NDM and PF-1 were obtained as described in Example 1.

The material retained in the aqueous phase also contained well resolved low molecular weight compounds as well as a substance(s) of very broad line spectrum reminiscent of that observed in PF-1. The results support applicants' previous conclusion that the adhesion inhibitory activity in CCM is not soluble in organic solvents.

Table 3 summarizes the differences between the present invention and the material of the '774 patent.

Further, PCT/US96/03978 (WO 96/30033) published application to Walker also discloses this extract from cranberry which is enriched for anti-adherence of bacteria activity. However, analysis of the composition of PCT/US96/03978 provides further confirmation that it is not the composition of the present invention, PF-1. The composition of the '978 application appear to be tannins, the approximate molecular weight of the disclosed compositions is 5000 although their mass spectrum gives a value of 577. The NMR spectra (proton and carbon) are different from those shown herein for the present invention.

As discussed herein above, U.S. Pat. No. 5,683,678 to Heckert et al discloses an oral composition containing anthocyanins isolated from cranberries and a composition having antiglucosyltransferase activity. Applicants have analyzed the composition of the present invention and it is not an anthocyanin and does not have antiglucosyltransferase activity.

These references describe compositions which are rich in polyphenols usually found in tannins and anthocyanins and molecules with a molecular weight range of 200–10,000.

Polyphenol Assay: A modified Folin-Denis test [Folin and Denis, 1912] was used to detect all hydroxylated phenolic compounds [Mehansho et al, 1987]. As a control standard commercially available tannin and anthocyanin was obtained from Sigma Chemical Co. (St. Louis, Mo.). The test was sensitive for phenolic compounds concentrations down to 0.02 mg/ml tanin in standard curves.

Results: NDM at 0.1 mg/ml concentration (repeated twice) showed less than 0.02 mg/ml of phenolic residues. Therefore, NDM does not contain phenolyic residues found typically in tannins and anthocyanins by this test.

AntiQlucosyltransferase Assay: This assay is based on formation of a sucrose polymer (dextran) insoluble in methanol from sucrose. If NDM has antigluscosyltransferase activity it will interfere with the assay.

Reagents: Glucosyltransferase enzyme solution was prepared from *S. sobrinus,* which produces four distinct glucosyltransferases, as follows. *S. sobrinus* 6715 bacteria were grown in defined medium [Terleckyj et al, 1975] for 16–18 hours. Cells were removed by centrifuagion and supernatants saved. The supernatants, on ice, were brought to 65% saturation with amonium sulfate and stirred gently overnight. Precipitates were collected and'dissolved in either 50 mM NaCl (pH 5.7) or 20 mM $PO_4$, 150 mM NaCl (pH 7.2). These precipitate samples provide a crude enzyme preparation. The samples are diaylyzed against PBS and protein content assayed and adjusted to 1 mg/ml to be used as the enzyme solution. Radiolabeled Sucrose-[$^{14}$C] was purchased from ICN (Irvine, Calif.). The sucrose was kept frozen in water until use. For the assay an aliquot was withdrawn and diluted with unlabeled sucrose to give a final concentration of 50 mM sucrose.

Assay: The assay described by Germaine et al [1974] was used with modification as follows. The enzyme solution is distributed to tubes (0.8 ml) and warmed to 37° C. for 15–20 minutes. To one set of tubes NDM was added to a final concentration of 1 mg/ml. In a parallel set of control tubes no NDM was added. Sucrose-$^{14}$C (0.2 ml) was added to all tubes and the tubes incubated at 37° C. At timed intervals aloquotes (0.1 ml; 1 minute, 2 minutes, 5, 10, 15, 20, 25, 30 minutes) were removed from the NDM tubes and control tubes and placed onto Whatman 3 MM filter disks. The filter disks were placed in cold methanol for 15 minutes to remove sucrose, the methanol wash repeated and the disks air dried and counted in a scintillation counter.

Results: In two separate assays, no difference was observed between the control and NDM tubes. The glucosyltransferase activity which catalyses synthesis of polysaccarhride from sucrose was not altered by the presence of NDM.

Example 7

Effect of PF-1 on Adhesion of Oral Bacteria

Most members of the bacterial genera in the dental plaque are capable of interacting with each other by specific mechanisms and these bacteria-bacteria interactions are now considered to be of paramount importance in the development of dental plaque [Kolenbrander et al, 1993]. Applicants' present invention provides that interference in the coaggregation between one bacterial species with another will hamper the development of dental plaque and that therefore in an embodiment PF-1 can be used as a medicament in prevention and/or treatment of plaque as shown in the Example herein below.

The oral cavity of mammals and of humans in particular is rarely colonized by *E. coli* nor is this bacterial species known to be involved in any diseases of the oral cavity. Therefore in order to study the effect of PF-1 on bacteria of the oral cavity, bacteria known to colonize the oral cavity were used as described herein below.

Initially the relationship between PF-1 anti-adhesion activity on P-fimbriae of uropathogenic *E. coli* and the anti-aggregation activity of selected coaggregating pairs of bacteria was established. Coaggregating pairs were selected to represent the bacteria that are involved in the various stages of dental plaque development and maturation. They included representatives of early colonizers (*S. oralis* 34 and *A. naeslundi* T14V); transition between early and late colonizers (*A. naeslundii* PK984 and *F. nucleatum* PK1909); and potentially periopathogenic bacteria (*P. gingivalis* and *F. nucleatum* PK1594).

In the first set of experiments, NDM (which contains PF-1) was tested to determine its effect on adhesion of oral bacteria. In these assays 40 pairs of bacteria that have been shown to inhabit the oral cavity were tested. The pairs were allowed to adhere to each other by forming aggregates followed by adding NDM to determine the minimal concentration required to completely reverse the coaggregation (adhesion; see FIG. 4). The results of the experiments performed are summarized in Table 4 herein below.

As shown in Table 4, the coaggregation of some oral bacteria pairs was highly sensitive to NDM. The coaggregation was reversed by concentrations as low as 1250 µg/ml.

The coaggregation of other bacterial pairs were less sensitive or insensitive (coaggregation was not reversed by concentrations as high as 5000 µg/ml). These results indicate that the various bacteria bind the inhibitor with various degrees of affinity. There is a wide range of receptor specificity of the adhesins carried by oral bacteria which is reflected in this finding.

In the second set of experiments PF-1 was employed and the results summarized in Table 5. As shown in Table 5, PF-1 was about ten times more active on a weight basis in reversing coaggregation between *A. naeslundii* and *F. nucleatum* as compared to NDM, showing that most of the inhibiting activity in NDM resides in PF-1. Adsorption of PF-1 with P fimbriated *E. coli* diminished the ability of the absorbed fraction to reverse coaggregation of the oral bacteria pair.

Table 5 also shows that alkaline treatments of PF-1 or acid treatment reduced the coaggregation activity of PF-1 while heating to 100° C. has no effect. Previous studies have shown that acid treatment of PF-1 has no effect on its anti-*E. coli* adhesion activity. The acid modified PF-1 looses its ability to bind to oral bacteria but retains its ability to bind P fimbriated *E. coli*.

Table 6 shows that significantly lower amounts of NDM were needed to inhibit coaggregation by preincubating the fraction with either bacterial species of *F. nucleatum* PK1909 and *A. naeslundii* PK984 pair of bacteria as compared to those needed to reverse preformed coaggregation between the bacterial pair. The results also show that the affinity of the inhibitor in NDM (which contains PF-1) to *F. nucleatum* is the same as that to *A. naeslundii* because the same NDM concentrations were needed to inhibit coaggregation when NDM was preincubated with either bacterial species. In contrast, NDM was more active in inhibiting coaggregation between *A. naeslundii* and *C. sputigena* when it was preincubated with the latter as compared to its inhibitory activity when preincubated with the former.

In Table 7, the anti-adhesion/aggregation activity of fractions from Example 3 are provided. The minimal inhibitory activity in µg/ml against P-fimbriated bacteria is compared to oral bacteria for each fraction. In general there was agreement. However as discussed above the fraction eluted in methanol did not have anti-inhibitory activity.

In summary, the adhesion (coaggregation) of 29 out of 37 pairs tested is completely reversed, showing that PF-1 will disturb the dental plaque. A hypothesis for the above observations can be made, but it is not to be construed as limiting the present invention to this one mode of action. The results are in line with the notion that the polymeric PF-1 targets it inhibitory activity to a defined range of bacterial adhesions. This notion is also evident from the analysis of the results of specific pairs of oral bacteria. For example, the adhesion of all 8 partners to *Fusobacterium nucleatum* PK 1904 is reversed by NDM, whereas that of only half of the partners to a different strain (PK 1594) of the same species is reversed by NDM. These results are analogous to *E. coli*, which produce multiple adhesins and only some of which, mainly those produced by the uropathogens, are inhibited by NDM.

Example 8

Further Method of Purification

For additional purification of PF-1 utilizing gel filtration the method as described herein above was modified as follows: cranberry juice concentrate (UPC# 94040 Lot #95071) obtained from Ocean Spray, (200 ml) was dialyzed against distilled water for seven days (changing the water twice daily), using diaylsis tubing with M.W. cut off of 12–15 kDa. The retentate was lyophylized to yield 3.44 g (1.7% w/v) of non-dialysable material (NDM) as described herein.

The NDM was then fractionated on Bio-Gel P-60 beads (BioRad, 130±40mm, exclusion limit of 60 kDa). The beads were soaked in PBS overnight and packed in a column 20 cm×2.5 cm and the column was loaded with 20 ml (10 mg/ml in PBS) NDM. All the material bound to about 5 cm of the top of the column. The column was washed with 100 ml PBS (at a flow rate of 1 ml/min.) and the water eluate discarded. Upon passing through the column 100 ml of 0.1 M $NH_4OH$, a second fraction was eluted. It was dialyzed against distilled water (1 liter) for 24 hours, lyophylized and the product designated PF-2. The minimal *E. coli* hemagglutination inhibitory concentration of PF-2 was 60–125 µg/ml, similar to that of PF-1 and represents an increased yield of about 2.5 to 5 fold as compared to NDM. The yield of PF-2 was 20–40% (w/w) which is considerably higher than that of PF-1 which was about 10% as described herein.

Example 9

Inhibition of Heamagglutination Between *H. pylori* and Human Erythrocytes by NDM.

*H. pylori* strain 25 was used in the experiments reported herein. It is a clinical isolate obtained from the Ezra Health Laboratory (Haifa, Israel). The strain is maintained by growing on Columbia agar (Oxoid Ltd., Basingstoke, Hants, UK) supplemented with yeast extract 0.2% and 10% egg yolk emulsion in plates under microaaerophilic conditions in anaerobic jars (CampyPakPlus, Beckton Dickinson Microbiology System, Cockeysville, Md.) at 37° C. After three days bacteria are harvested from the agar plates for use. The bacteria are suspended in PBS to 1.0 O.D. at 660 nm which is equivalent to approximately $5 \times 10^8$ CFU/ml.

As described for the hemagluttination assay, bacteria were grown on agar for three days, scraped from agar and suspended in phosphate buffer saline to a density of 1.0 OD. Hemagglutination activity and its inhibition by NDM were done as described previously (Zafriri et al, 1989). The results are shown in Table 9 and demonstrate that NDM will inhibit heamagglutination by *H. pylori*.

Example 10

Inhibition of Adhesion of *Helicobacter pylori* to Human Gastric Mucus by NDM

Preparation of microtiter plates containing immobilized human mucus: Human mucin (S-11/97) was obtained from the Department of Pathology, RamBam Hospital, Haifa. The mucin was dissolved in 0.1 M NaCl to obtain a 10% (V/V)

solution. 1 M NaOH was added to reach pH 7.0 and incubated overnight at 4° C. The suspension was then centrifuged for 10 minutes at 10,000×G and to the sediment mucin ethanol 60% (V/V) was added. After 30 minutes at 4° C., the mucus was sedimented by centrifugation and re-dissolved in 0.1 M NaCl to a concentration of ipg/ml protein. Coating of wells with mucin was done by adding 0.1 ml of mucin to each well of 96-microtiter plates, incubating for 24 hours at 37° C. and washing with 20 mM phosphate buffer saline (PBS) [Burger et al, 1998].

Determination of adhesion of *H. pylori* to immobilized mucin and its inhibition by NDM: 0.01 ml NDM (1 mg/ml) in PBS or PBS only was added to 0.1 ml bacterial suspension and the mixture was placed into the wells containing the immobilized human mucin. After 90 minutes incubation the wells were washed free of non-adherent bacteria and the amount of bacteria remaining adherent was determined by measuring urease activity of the bound bacteria. Urease activity was monitored over three hours time by adding to each well at the desired time phenol red (7 mg/ml) and urea (330 mico mol /ml) followed by recording the development of color at 560 nm. Control experiments showed that NDM has no effect on the urease activity of the bacteria and that preincubation of the mucin layer with NDM followed by washing off excess NDM had no effect on *H. pylori* adhesion.

The results (FIG. 9) show the urease activity of *H. pylori* bound to mucin after incubation with and without NDM, as described above. It can be seen that very little activity was detected in wells incubated with the bacteria in the presence of 0.1 mg/ml NDM. Therefore there was reduced adhesion of the *H. pylori* to the human mucin.

Throughout this application, various publications, including United States patents, are referenced by citation or number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

Inhibition of Coaggregation/Adhesion Studies

| Fraction | Minimum Adhesion-Inhibitory Conc.* HA: P-fimbriated | Minimum Adhesion-Inhibitory Conc.* Coag: Oral Bacteria |
|---|---|---|
| Cranberry Juice | 1:8–1:16 | n.d. |
| Non-dialyzable material (NDM) | 50–200 µg/ml | 50–200 µg/ml |
| PF-1 | 10–40 µg/ml | 12–50 µg/ml |

*Dilution or concentration (µg/ml) needed to complete inhibition of hemagglutination (HA) or coaggregation (Coag) of oral bacteria.

TABLE 2

Inhibition of Coaggregation/Adhesion Studies

| Fraction | HA* (µg/ml) | Coag* (µg/ml) |
|---|---|---|
| PF-1 | 10–40 | 12–50 |
| Unfractionated CCM | 400–1600 | 500–1000 |
| Butanol Soluble | 3000 | 1000–2000 |
| Ethyl acetate soluble | 3000 | 500–1000 |
| Retained in aqueous phase | 400 | 500–1000 |

*See legend to Table 1.

TABLE 3

| PROPERTY OF MATERIAL | PF-1 | '774 Patent and PCT/03978 |
|---|---|---|
| Molecular Weight/Size | High/Big | Low/Small |
| Method to Obtain | Dialysis and gel filtration | Extraction by organic solvents |
| Solubility in organic solvents | Not soluble | Soluble |
| Target System | Dental Plaque | Oral Surfaces |
| Target Bacteria | Oral Bacteria | Not specified |
| Bacteria Tested | Oral Bacteria (>20 species) and P-fimbriated | *E. coli* |
| Effect on adhesion of Type 1 P-fimbriated bacteria | None | Positive |
| Ability of bacteria tested to reside in oral cavity | All | None |
| Type of effect on adhesion | Reversal and Inhibition | Inhibition |
| Adhesion system tested | Interspecies and intraspecies adhesion of oral bacteria | *E. coli* adhesion to erythrocytes and bladder cells |
| Relevance of systems tested to dental hygiene | Relevant | Not relevant |

TABLE 4

REVERSAL OF COAGGREGATION
Table 4: Effect of nondialysable materiat (NDM) obtained from cranberry on intergeneric adhesion (coaggregation) of oral bacteria

| Bacterial partners tested | | Concentration of NDM (mg/ml) needed to reverse coaggregation* |
|---|---|---|
| *Fusobacterium nucleatum* PK1909 | *Actinomyces naeslundii* PK984 | 1.25 |
| | *Actinomyces naeslundii* PK29 | 1.25 |
| | *Gemella morbilorum* PK509 | 1.25 |
| | *Actinomyces naeslundii* PK947 | 2.50 |
| | *Streptococcus sanguis* J22 | >2.50 |
| | *Porphiromonas gingivalis* PK1924 | 2.50 |
| | *Streptococcus oralis* SS34 | 2.50 |
| *Fusobacterium nucleatum* PK1904 | *Actinomyces israelii* PK14 | 2.50 |
| | *Actinomyces naeslundii* PK947 | 1.25 |
| | *Capnocytophaga ochracea* ATCC33596 | 1.25 |
| | *Actinomyces naeslundii* PK29 | 2.50 |
| | *Gemella morbilorum* PK509 | 1.25 |
| | *Prevotella denticola* PK1277 | 2.50 |
| | *Actinomyces naeslundii* T14V | 1.25 |
| | *Actinomyces naeslundii* ATCC12104 | 1.25 |
| *Fusobacterium nucleatum* PK1594 | *Actinomyces naeslundii* PK29 | 2.50 |
| | *Actinomyces naeslundii* PK984 | 2.50 |
| | *Actinomyces israelii* PK14 | 2.50 |
| | *Actinomyces naeslundii* PK947 | 2.50 |
| | *Porphiromonas gingivalis* PK1924 | 2.50 |
| | *Streptococcus gordonii* ATCC51656 | 1.25 |
| | *Capnocytophaga ochracea* ATCC33596 | 1.25 |
| | *Actinomyces naeslundii* T14V | 1.25 |
| | *Streptococcus oralis* SS34 | >2.50 |
| | *Actinomyces naeslundii* ATCC12104 | >2.50 |
| | *Actinomyces israelii* PK16 | 2.50 |
| *Capnocytophaga sputigena* ATCC33612 | *Actinomyces naeslundii* PK984 | 1.25 |
| | *Actinomyces israelii* PK14 | 2.50 |
| | *Actinomyces naeslundii* PK947 | 2.50 |
| | *Actinomyces naeslundii* PK29 | 2.50 |
| | *Actinomyces naeslundii* ATCC12104 | >2.50 |
| *Actinobacilus actinomycetemcomitans* JP2 | *Actinomyces naeslundii* PK984 | >2.50 |
| *Prevotella intermedius* PK1511 | *Actinomyces naeslundii* PK984 | 1.25 |
| *Actinomyces naeslundii* PK947 | *Capnocytophaga sputigena* ATCC33612 | >2.50 |
| | *Streptococcus oralis* SS34 | >2.50 |
| *Prevotella loescheii* PK1295 | *Actinomyces naeslundii* PK984 | >2.50 |
| | *Actinomyces israelii* PK14 | >2.50 |

*>not completely inhibited at 2.50 mg/ml

TABLE 5

Table 5: Effect of various treatments on the ability of cranberry-derived fractions to reverse coaggregation between *Fusobacterium nucleatum* PK1909 and *Actinomyces naeslundii* PK984

| Treatment of Cranberry fraction | Concentration (mg/ml) of cranberry-derived fractions needed to reverse coaggregation |
|---|---|
| NDM, untreated | 1.25 |
| PF-1, untreated | 0.15 |
| PF-1, 100° C., 30 minutes | 0.15 |
| PF-1, 0.1 N HCl, 30 minutes | 1.25 |
| PF-1, 0.1 N NaOH, 30 minutes | 1.25 |
| Trypsin, 100 µg/ml, 30 minutes | 0.15 |
| PP-1, adsorbed with P. fimbriated *E. coli* | >1.25* |

*lack of inhibitory activity at 1.25 mg/ml

TABLE 6

Comparison between the ability of cranberry-derived PF-1 to inhibit and to reverse coaggregation of oral bacteria

| Coaggregating Bacterial pairs | | PF-1 fraction | | |
|---|---|---|---|---|
| | | Preincubated with: | Added to performed | PF-1 (mg/ml) needed to inhibit or reverse |
| A | B | A    B    coaggregates | | coaggregation |
| *A. naeslundii* PK984 | *F. nucleatum* PK1909 | + | | 0.037 |
| | | + | | 0.037 |
| | | | + | 1–5.0 |
| *A. israelii* PK14 | *C. sputigena* ATCC33612 | + | | 0.15 |
| | | + | | 0.075 |
| | | | + | 2–5.0 |

TABLE 7

Minimal Inhibitory Activity (MIA; μg/ml) Obtained from Iron free PF-1 and Other Fractions Obtained by Reverse Phase Chromatography, Acetylation and Acid Methanolysis.

Figure 2C:
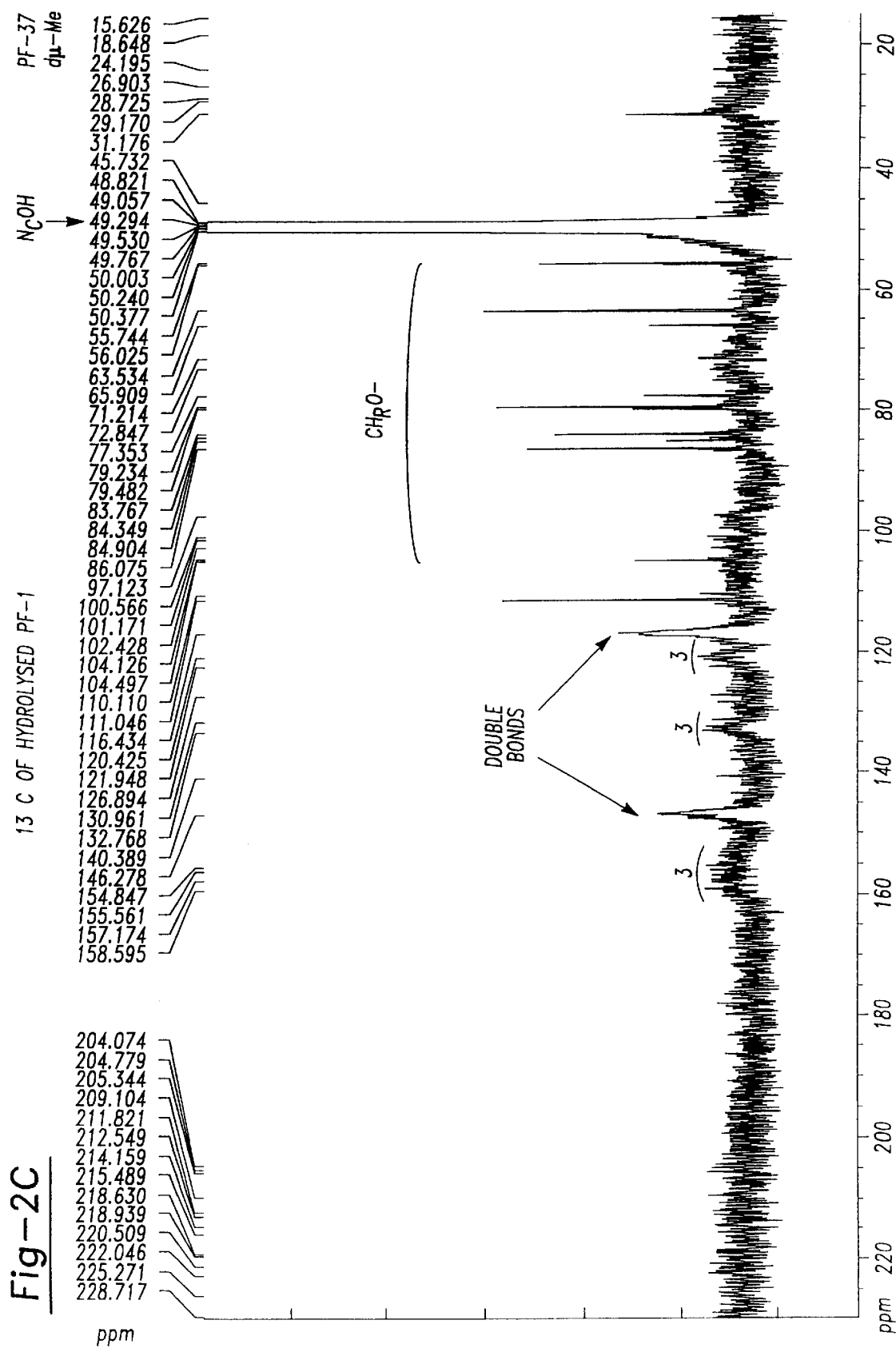

| Fraction | Treatment | MIA of P-fimbriated bacteria | MIA of Oral bacteria |
| --- | --- | --- | --- |
| PF-1 | Untreated (FIG. 2A) | 10–25 | 12–50 |
| PF-1-20 Iron free | 8-hydroxyquinoline (FIG. 2A) Reverse Phase Chromatography of PF-1-20: | 25–35 | 25–50 |
| PF-1-20/1 | water elution | 40 | 50 |
| PF-1-20/2-5 | 20%–80% methanol | 300–2000 | 50–2000 |
| PF-1-31 | Acetylation | NT | >400 |
| PF-1-26 | Acid Methanolysis (8 hours) (FIG. 2C) | 200–600 | 100–220 |
| PF-1-37 | Acid Methanolysis (30 hours) | 200–600 | 100–300 |

TABLE 8

ACTIVITY OF CRANBBRRY-DERIVED FRACTIONS

| | Minimal inhibitory concentration mg/ml | |
| --- | --- | --- |
| Fraction | E. coli P adhesion | Oral bacteria coaggregation. |
| NDM | 0.200–0.150 | 0.200–0.150 |
| PF-1 | 0.125–0.050 | 0.120–0.050 |
| PF-2 | 0.125–0.050 | 0.120–0.050 |

TABLE 9

Effect of PF-1 on adhesion of *Helicobacter pylori*

| Strain | Source | Hemagglutinating titer | Concentration of PF-1 needed to inhibit hemagglutination mg/ml |
| --- | --- | --- | --- |
| #25 | Clinical isolate | 1:16 | 0.25 |

REFERENCES

Anstee and Tanner, 1974. The distribution of blood-group antigens on butanol extraction of human erythrocyte "Ghosts", Biochem. J., 138:381–386.

Aronson, et al., 1979. Prevention of *E. coli* colonization of the urinary tract by blocking bacterial adherence with α-methyl-D-mannopyranoside. J. Infect. Dis. 139:329–332.

Athaman and Ofek, 1988. Enzyme-linker immunosorbent assay for quantitation of attachment and ingestion stages of bacterial phagocytosis Infect. Immun., 26:62–66.

Avorn et al. 1994. Reduction of bacteriuria and pyuria After Ingestion of Cranberry Juice. JAMA 271(10):751–754.

Blaser, 1996. The Bacteria Behind Ulcers. Scientific American, February, pgs. 104–107.

Boren, et al., 1993. Attachment of *Helicobacter pylori* to human gastric epithelium mediated by blood group antigen. Science 262:1892–1895.

Boren and Falk, 1995. *Helicobacter pylori* binds to blood group antigens. Scientific American Science and Medicine. September/October 28–37.

Burger et al., 1998. High Molecular weight constituent of cranberry juice inhibits the adhesion of *Heliobacter phlori* to human gastric mucin. Abstract, 11th Mediterranean Congress of Chemotherapy, TelAviv.

Cover and Blaser, 1995. *Helicobacter pylori:* a bacterial cause of gasrtritis, peptic ulcer disease, and gastric cancer. A. S. M. News 61:21–26.

DeMan, et al., 1987. Receptor specific agglutination tests for detection of bacteria that bind globoseries glycolipids. J. Clin. Microbiol. 25:401–406.

Dubois et al. 1956. Colorimetric Method for Determination of Sugars and Related Substances. Anal. Chem. 28:350–356.

Duguid and Old, 1980. Adhesive properties of enterobacteriaceae. In: *Bacterial Adherence*, (Beachey E. H., ed.), Receptors and Recognition, Series B, Vol. 6, pp 187–217, Chapman and Hall Ltd., London. Dunn et al., 1997. Helicobacter pylori. Clin. Microbiol. Rev. 10:720–741.

Dzink et al., 1988. The predominant cultivable microbiota of active and inactive lesions of destructive periodontal diseases. J Clin Periodontol. 15:316–323.

Dzink et al., 1985. Gram-negative species associated with active destructive periodontal lesions. J Clin Periodontol 12:648–659.

Firon, et al., 1984. Carbohydrate-binding sites of the mannose-specific fimbrial lectins of enterobacteria. Infect. Immun. 43:1088–1090.

Folin and Denis, 1912. On phosphotungstic-phophomolybdic compounds as color reagents. J. Biol. Chem. 12:239–243.

Germaine et al., 1974. Rapid filter paper assay for the dextransucrase activity from *Streptococcus mutans*. J. Dent. Res. 53(6):1355–1360.

Gibbons, et al., 1991. Delineation of a segment of adsorbed salivary proline-rich proteins which promotes adhesion of *Streptococcus gordonii* to apatitic surfaces. Infect Immun 59:2948–2954.

Gibbons and van Houte, 1975. Bacterial adherence in oral microbial ecology. Ann Rev Microbiol 29:19–44.

Goldhar, 1995. Erythrocytes as target cells for detection and characterization of bacterial adhesins. Vol.253. In: Methods of Enzymology. Adhesion of Microbial Pathogens. R. J. Doyle and I. Ofek, ed. Academic Press Inc. p. 43–50.

Grunberg, et al., 1994. Blood group NN dependent phagocytosis mediated by NFA-3 heamagglutinin of *Escherichiae coli*. Immunol. & Infect. Dis. 4:28–32.

Helrich (editor), 1990. Official Methods of Analysis of the Association of Official Analytical Chemists. pg. 703, section 952.03.

Lee A, Fox J, adn Hazell S. 1993. pathogenicity of Helicobacter pylori: a perspective. Infect. Immun. 61:1601–1610.

Kolenbrander, 1988. Intergeneric coaggregation among human oral bacteria and ecology of dental plaque. Annu. Rev. Microbiol. 42:627–656.

Kolenbrander et al., 1989. Coaggregation of *Fusobacterium nucleatum, Selenomonas flueggei, Selenomonas infelix, Selenomonas noxia,* and *Selenomonas sputigena* with strains from 11 genera of oral bacteria. Infect. Immun., 57:3194–3203.

Kolenbrander et al., 1993. Coaggregation: Specific adherence among human and plaque bacteria. FASEB J 7:406–413.

Kolenbrander and London, 1993. Adhere today, here tomorrow: Oral bacterial adherence. J Bacteriol 175:3247–3252.

Leibusor et al., 1996. Cranberry juice inhibits coaggregation of oral bacteria. Presented at the annual meeting of the International Association of Dental Research (IADR), San Francisco, Calif., Mar. 14–17, 1996.

Lynn, et al., 1982. Factors affecting excretion of human urinary Tamm-Horsfall glycoprotein. Clinical Science 62:21–26.

Mehansho et al., 1987. Dietary tannins and salivary prolin-rich proteins: Interactions, induction, and defense mechanisms. Ann. Rev. Nur. 7:423–440.

Moore and Moore, 1994. The bacteria of periodontal diseases. Periodontol 2000 5:66–77.

Nyvad and Kilian, 1990. Comparison of the initial streptococcal microflora on dental enamel in caries-active and in caries-inactive individuals. Caries Res 24:267–272.

Ofek, 1995. Enzyme-linked immunosorbent based adhesion assays. In: Doyle, R. and I. Ofek. (eds) Adhesion of Microbial Pathogens. Methods in Enzymology. 253: 528–536. Academic Press, N.Y.

Ofek and Doyle, 1994. Bacterial Adhesion to Cells and Tissues, Chapman and Hall Ltd., London. pgs. 357–365.

Ofek et al., 1991. Anti-*Escherichia coli* adhesion activity of cranberry and blueberry juices. New Eng. J. Med. 324: 1599.

Ofek et al., 1993. Effect of various juices on activity of adhesins expressed by urinary and nonurinary isolates of *Escherichiae coli*. In America's Foods Health Messages and claims: Scientific, Regulatory, and Legal Issues (J. Tilloston, ed) CRC press, Inc. pp 193–201.

Ofek, et al., 1996. Toward anti-adhesion therapy for microbial diseases. Trends Microbiol. 4: 297–299

Parkkinen, et al., 1988. Identification of factors in human urine that inhibit the binding of *Escherichia coli* adhesins. Infect. Immun. 56:2623–2630.

Savitt and Socransky, 1984. Distribution of certain subgingival microbial species in selected periodontal conditions. J Periodontal Res. 19:111–123.

Schmidt and Sobota, 1988. An examination of the anti-adherence activity of cranberry juice on urinary and nonurinary bacterial isolates. Microbios 55:173–181.

Slots, 1977. Microflora in the healthy gingival sulcus in man. Scand J Dent Res. 85:247–254.

Sobota, 1984. Inhibition of bacterial adherence by cranberry juice: Potential use for treatment of urinary tract infection. J. Urol. 131:1031–1016.

Socransky, et al., 1982. Present status of studies on microbial etiology of periodontal diseases. In Genco R, Mergenhagen SE. (Eds). *Host-parasite Interactions in Periodontal Disease*. American Society for Microbiology, Washington, DC.

Terleckyj, et al., 1975. Growth of several cariogenic strains of oral streptococci in a chemically defined medium. Infect. Immun. 11(4):649–655.

van Houte, 1980. Bacterial specificity in the etiology of dental caries. Int Dent J. 30:305–326.

Wadstrom, 1995. An update on *Helicobacter pylori*. Curr. Opinions in Gastroenterol. 11:69–75.

Weiss, et al., 1990. Identification of the rhamnose-sensitive adhesion of *Capnocytophaga ochracea* ATCC 33596. Archs Oral Biol 35 suppl:127S–130S.

Weiss, et al., 1989. Fimbriae-associated adhesion of *Bacteroides loescheii* that recognizes receptors on prokaryotic and eucaryotic cells. Infect Immun. 57:2912–2913.

Weiss et al., 1987. Characterization of lectin-like surface components on Capnocytophaga ochracea ATCC33596 that mediate coaggregation with gram-positive oral bacteria. Infect. Immun. 55:1198–1202.

Zafriri et al., 1989. Inhibitory activity of cranberry juice on adherence of type 1 and type P fimbriated *Escherichia coli* to eucaryotic cells. Ant. Microbial Agt. Chem. 33:92–98.

What is claimed is:

1. A fortified food composition providing antimicrobial-adhesion activity comprising a suitable food carrier and an effective amount of an isolated adhesion inhibitory water extract fraction from Vaccinium having (a) a molecular weight of 14,000 kDa as determined by dialysis with a 14,000 kDa molecular weight cut off;

(b) coaggregation reversal and coaggregation inhibition activity against oral bacteria;

(c) an elemental analysis of carbon 43–51%, hydrogen 4–5%, no nitrogen, no sulfur and no chlorine;

(d) a nuclear magnetic resonance (NMR) line spectrum as set forth in FIGS. 2A and 2B;

(e) an ultraviolet spectrum with an absorption peak at 280 nm in neutral or acidic pH solution which is absent in alkali solutions; and (f) an adhesion inhibitory activity against P fimbriated bacteria.

2. The composition as set forth in claim 1 wherein the food carrier is a fruit juice.

3. The composition as set forth in claim 2 wherein the fruit juice is cranberry juice.

* * * * *

UNITED STATES PATENT AND TRADEMARK OFFICE
CERTIFICATE OF CORRECTION

PATENT NO. : 6,303,125 B1  Page 1 of 1
DATED : October 16, 2001
INVENTOR(S) : Ofek et al.

It is certified that error appears in the above-identified patent and that said Letters Patent is hereby corrected as shown below:

<u>Column 28,</u>
Line 27, should read as follows:

-- (a) a molecular weight greater than or equal to 14,000 kDa as determined by dialysis with a 14,000 kDa molecular weight cut off --

Signed and Sealed this

Eighteenth Day of June, 2002

*Attest:*

*Attesting Officer*

JAMES E. ROGAN
*Director of the United States Patent and Trademark Office*